United States Patent
Wilson et al.

(10) Patent No.: US 9,151,694 B2
(45) Date of Patent: Oct. 6, 2015

(54) SYSTEM AND METHOD OF HIGH RESOLUTION FIBER OPTIC INSPECTION

(71) Applicant: FiberQA, LLC, Old Lyme, CT (US)

(72) Inventors: Douglas H. Wilson, Mystic, CT (US); Jan R. Endresen, Rye, NY (US)

(73) Assignee: FIBERQA, LLC, Old Lyme, CT (US)

( * ) Notice: Subject to any disclaimer, the term of this patent is extended or adjusted under 35 U.S.C. 154(b) by 123 days.

(21) Appl. No.: 13/785,940

(22) Filed: Mar. 5, 2013

(65) Prior Publication Data
US 2013/0229650 A1 Sep. 5, 2013

Related U.S. Application Data

(60) Provisional application No. 61/606,944, filed on Mar. 5, 2012.

(51) Int. Cl.
| | |
|---|---|
| *G01M 11/00* | (2006.01) |
| *G02B 6/38* | (2006.01) |
| *B08B 1/00* | (2006.01) |
| *B08B 11/00* | (2006.01) |
| *G01B 11/30* | (2006.01) |
| *G01N 21/88* | (2006.01) |
| *G01N 21/94* | (2006.01) |
| *G01N 21/95* | (2006.01) |

(52) U.S. Cl.
CPC .......... *G01M 11/31* (2013.01); *B08B 1/00* (2013.01); *B08B 11/00* (2013.01); *G01B 11/30* (2013.01); *G01N 21/88* (2013.01); *G01N 21/94* (2013.01); *G02B 6/385* (2013.01); *G02B 6/3866* (2013.01); *B08B 2240/02* (2013.01); *G01M 11/3145* (2013.01); *G01N 2021/9511* (2013.01)

(58) Field of Classification Search
None
See application file for complete search history.

(56) References Cited

U.S. PATENT DOCUMENTS

| | | | |
|---|---|---|---|
| 5,179,419 A * | 1/1993 | Palmquist et al. | 356/73.1 |
| 6,178,285 B1 * | 1/2001 | Csipkes et al. | 385/147 |
| 6,449,795 B1 * | 9/2002 | Sato | 15/210.1 |

(Continued)

FOREIGN PATENT DOCUMENTS

WO 2013134278 A1 9/2013

OTHER PUBLICATIONS

PCT/US2013/029144, "International Application Serial No. PCT/US2013/029144, International Search Report and Written Opinion mailed Jun. 21, 2013", FIBERQA, LLC, 10 pages.

(Continued)

*Primary Examiner* — Gordon J Stock, Jr.
(74) *Attorney, Agent, or Firm* — GTC Law Group LLP & Affiliates

(57) ABSTRACT

This disclosure concerns a cleaning and inspection system for fiber optics that is rapid, reliable and useful for various types of fiber optics. In an embodiment, the system includes a wide field of view (FOV) camera to image the ferrule and rapidly locate the fiber ends and a narrow FOV camera to provide detailed inspection of fiber ends. A cleaning module with a cleaning tip and a cleaning media that is drawn through the tip is used to clean the fiber ends. Images captured by the dual cameras are automatically enhanced and analyzed to determine the effectiveness of the cleaning process and to identify the types and quantity of defects present. In another embodiment, a single higher resolution camera is provided with a lens that can image an entire fiber array and yet enable defects to be detected by analysis of sub-images of each fiber in the fiber array.

18 Claims, 28 Drawing Sheets

(56) References Cited

U.S. PATENT DOCUMENTS

| | | | | |
|---|---|---|---|---|
| 6,466,366 | B1* | 10/2002 | Dominique | 359/379 |
| 6,705,767 | B1* | 3/2004 | Dean et al. | 385/85 |
| 6,758,605 | B1* | 7/2004 | Villemaire et al. | 385/85 |
| 7,113,273 | B2* | 9/2006 | Pahk et al. | 356/237.1 |
| 7,221,805 | B1 | 5/2007 | Bachelder | |
| 7,356,236 | B1* | 4/2008 | Huang et al. | 385/134 |
| 7,808,624 | B2* | 10/2010 | Wells | 356/73.1 |
| 7,837,801 | B2 | 11/2010 | Christopher et al. | |
| 8,699,012 | B2* | 4/2014 | Duis et al. | 356/73.1 |
| 8,988,670 | B2* | 3/2015 | Zhou et al. | 356/73.1 |
| 2002/0131748 | A1* | 9/2002 | Sato | 385/134 |
| 2003/0098045 | A1* | 5/2003 | Loder et al. | 134/8 |
| 2004/0125366 | A1 | 7/2004 | Kiani et al. | |
| 2004/0165181 | A1* | 8/2004 | Kume et al. | 356/237.2 |
| 2008/0304051 | A1* | 12/2008 | Wells | 356/73.1 |
| 2009/0219434 | A1* | 9/2009 | Kauhanen | 348/345 |
| 2011/0085158 | A1 | 4/2011 | Motter et al. | |
| 2011/0085159 | A1* | 4/2011 | Levin et al. | 356/73.1 |
| 2011/0150395 | A1 | 6/2011 | Steinblatt et al. | |
| 2011/0303241 | A1* | 12/2011 | Tourigny | 134/9 |
| 2013/0194566 | A1* | 8/2013 | Schell et al. | 356/73.1 |
| 2014/0211200 | A1* | 7/2014 | Kim | 356/73.1 |
| 2014/0268114 | A1* | 9/2014 | Zhou et al. | 356/73.1 |

OTHER PUBLICATIONS

PCT/US2013/029144, International Application Serial No. PCT/US2013/029144, International Preliminary Report on Patentability With Written Opinion mailed Sep. 18, 2014, FIBERQA, LLC, 6 Pages.

\* cited by examiner

Fig. 17

SYSTEM AND METHOD OF HIGH RESOLUTION FIBER OPTIC INSPECTION

CROSS-REFERENCE TO RELATED APPLICATIONS

This application claims the benefit of the following provisional application, which is hereby incorporated by reference in its entirety: U.S. Provisional Application 61/606,944, filed Mar. 5, 2012.

This application is also related to the following U.S. patent, each of which is incorporated by reference herein in its entirety: U.S. Pat. No. 6,758,605.

BACKGROUND

1. Field

The methods and systems described herein generally relate to enhanced fiber optic cleaning and inspection methods and systems.

2. Description of the Related Art

In fiber optic systems, it is important to provide very low losses of light at junctions between fibers and other optical devices, while retaining the flexibility of field interconnections. As a result, the end faces of fiber optic connectors must be smoothly polished to reduce scratches that scatter light and cleaned to remove contaminants and particles that block or scatter light. To verify the optical quality of the end face of the fiber optic connector, the fiber optic connector is cleaned and then inspected. Given that fibers have cores that can range in size from approximately 7 micron to 3 mm, very small defects can contribute to unacceptable losses so that the cleaning and inspection processes must be capable of reliably removing and detecting micron sized defects. For ease of handling and proper alignment, fibers are typically mounted into a ferrule that is larger and more durable. Ferrules can include multiple fibers such as for fiber arrays. The ferrule is typically mounted into a connector for connecting to another ferrule with mating fiber optics. The ferrule and connector must be cleaned and inspected after the fibers have been mounted. In addition to inspecting the fiber end faces, some standards and customers require the inspection of the ferrule region for contamination and/or scratches. This inspection requires a much larger (up to a few millimeters) Field of View, but generally at slighter lower resolution than is required for the fiber end face inspection.

In arrays of fibers, the inspection system needs to be able to locate the fibers within the ferrule to assist the inspection process. Typically an optics based search method along with known dimensional information associated with the ferrule is used to locate the fibers. However, given the large size of the ferrule relative to the size of the fiber, the magnification and field of view of the optics used to find the fiber is different from the optics used to characterize the defects on the fiber end. Cleaning can be performed before or after the fibers have been found. In an automated process, the method for finding the fibers, cleaning the fibers and then identifying defects can determine the speed and efficiency of the inspection process.

U.S. Pat. No. 7,837,801 describes a method and apparatus for cleaning an optical fiber using a cleaning wipe. A variety of cleaning techniques using cleaning wipes are disclosed. Automated inspection is not included with the automated cleaning.

United States Patent publication 2011/0085159 provides a handheld fiber optics inspection probe with a lens and a camera with autofocus to capture an image of the fiber optic. Cleaning is not provided along with the inspection probe and the inspection probe is not automated for inspecting arrays of fiber optics. Because the inspection probe is handheld, a single set of optics is provided and the finding of the fiber is left to the operator.

United States Patent publication 20040125366 discloses a system for automated inspection of fiber. The system includes mechanisms to automatically center, focus a lens, and capture images of ends of fiber optics to assess defects that are present. The inspection system can be combined with a cleaning system on a portable cart to clean the fiber optics prior to inspection. However, the cleaning and inspections systems are not connected so that recontamination is possible. In addition, the system does not include a way to automatically identify the positions of the fibers, instead the system relies on input dimensions. The use of lower magnification optics to provide a wider field of view for finding the fibers is not discussed.

United States Patent publication 20110150395 describes an automated system for fiber severing to cut the fibers in a connector to the same length to prepare the connector for polishing. Wherein the relative position of the ends of the fiber optics is inferred by determining the positions of the ferrule shoulders surrounding the fiber optics using a camera and image analysis. The system provided uses a video camera located at the side so that length of the fibers can be determined; as such this camera system is not capable of investigating defects on the ends of the fibers.

Therefore there remains a need for an improved method for performing automated finding of fiber end faces, cleaning of the fiber end faces, fiber optic connector or other fiber optic components and inspection for defects in a fast and efficient manner.

SUMMARY

The present disclosure provides a cleaning and inspection system for fiber optics that is rapid and reliable and can be used for various types of fiber optic components, in order to clean ends of optical fibers and in some cases the surrounding ferrule. The system includes dual cameras to identify the locations of the optical fibers and then to inspect the ends of the optical fibers for defects. A wide field of view (FOV) camera is provided for imaging the ferrule so that the fiber ends can be rapidly located. In addition, this wide FOV camera image may be used for inspecting the ferrule for defects. A cleaning module with a cleaning tip that uses a cleaning media that is drawn through the cleaning tip is used to clean the ends of the fiber optic component at the identified locations. A narrow FOV camera, with higher resolution, is provided for detailed inspection of the optical fiber ends following cleaning. Images captured by the dual cameras are enhanced and analyzed to determine the effectiveness of the cleaning process and to identify the types and quantity of defects present. An automated assessment of the fiber optic component is provided.

In an aspect of this disclosure, an integrated system for optical fiber end face inspection and cleaning is described. The system may include a first camera adapted to image a ferrule. The second camera is positioned in an estimated fiber location based on a ferrule image acquired by the first camera, wherein the second camera is adapted to image at least one fiber of the ferrule. A cleaning module of the system cleans an imaged fiber using a tip with a cleaning media that is moved relative to the fiber. In some embodiments of the system, a processor is included that is adapted to analyze a fiber image acquired by at least one of the first camera and the second camera and determine the presence of a defect.

The system may include a motion control system adapted to position the first camera at a ferrule location based on part specific configuration data. The motion control system may position the second camera at the estimated fiber location. The motion control system may automatically center the second camera based on execution of a fiber finding algorithm executed on an image captured by the first camera. The motion control system may move one or more of the first camera, the second camera, and the cleaning module in a plurality of motion axes, such as x, y, and z axes. The first and second cameras may each include an autofocus facility. The autofocus facility may include at least one of moving a camera, moving an element in a lens or changing an optical power in a variable optical power element. The tip may be adapted to receive the cleaning media and to make contact with at least one of the optical fiber and the ferrule. The system may further include a light source that is controlled to inject light into a first end of an optical fiber or set of optical fibers under test, wherein the first camera is used to verify an output light at a second end of the optical fiber or set of optical fibers. The first and second cameras may include fixed focus distances and focus adjustment may be provided by the motion control system moving the cameras to focus on the ferrule or fiber. The system may further include at least one light source to illuminate at least one of the ferrule and the optical fiber end face. The at least one light source may include at least one of: a bright field light, a dark field light, a polarized light, an edge light, a broad spectrum light, a narrow spectrum light, a visible light, an infrared light, and an ultraviolet light.

The cleaning module may include a circulation facility for circulating the cleaning media within a housing of the cleaning module and on the tip to expose an unused portion of cleaning media that contacts the optical fiber end face, wherein new unused cleaning media is continually provided while used cleaning media is continually carried away. A motion control system may control a cleaning motion of the tip. The tip may be a rectangular tip adapted for cleaning optical fiber end faces of MT, other parallel optics, or other array style, multiple fiber connectors. The cleaning media may be selected from one or more of a polyester thread, a polyester fabric, a nylon thread and a nylon fabric. The cleaning module may be positioned outside of the field of view of the first and the second camera, or it may be adapted to be positioned along the same optical axes as at least one of the first camera and the second camera. The cleaning module may include a force controller that controls the force pushing the cleaning tip against the optical fiber. Such force control may be active, by means of force feedback and motion control, or passive by means of a spring. The tip may be rotated back and forth about the long axis of the tip. The tip may be moved in an oscillatory movement that begins at one corner of an array of optical fiber end faces, crosses the array and ends at an adjacent corner of the array. The tip may be moved in a line down an array of optical fiber end faces combined with an overlaid circular cleaning path. The tip may be moved in a side-to-side motion, normal to the long axis of an MT or array ferrule, while the thread is pulled along the long axis. The tip may be removed from contact with the optical fiber end faces and repositioned before continuing with a cleaning process or repeating a cleaning process.

In an aspect of this disclosure, a method for optical fiber end face inspection and cleaning may include imaging a ferrule with a first camera, positioning a second camera in the location of at least one fiber for inspection at a fiber location that is estimated based on a ferrule image acquired by the first camera, imaging at least one fiber of the ferrule with the second camera, and processing at least one fiber image acquired by at least one of the first camera and the second camera to determine the presence of a defect, and if a defect is detected or a threshold of defect detection is reached, cleaning the at least one fiber with a cleaning module that comprises a tip with a cleaning media that is moved relative to the fiber to clean the fiber. The method may further include re-imaging the at least one fiber of the ferrule with the second camera to acquire at least one fiber image, processing the at least one fiber image to determine the presence of a defect, and if a defect is detected, re-cleaning the fiber. The method may further include automatically focusing at least one of the first camera and the second camera with an autofocus facility, wherein the autofocus facility comprises at least one of moving the camera, moving an element in a lens or changing the optical power of a variable optical power element, or is provided by moving an image sensor in the camera. The method may further include determining a focus quality by evaluating the relative contrast within a series of captured images with different focus settings and selecting the focus setting with the highest contrast or by making a phase contrast measurement on a portion of the incoming light that is diverted with a beam splitter. Determining the presence of a defect may include identifying a location, measuring the defect, calculating an occluded area of the fiber, a contrast of each scratch and particle, and computing a total area of defects on the optical fiber end face (e.g. in order, for example, to calculate at least one of an insertion loss and a return loss).

In an aspect of this disclosure, a system for optical fiber end face inspection may include a camera adapted to image an optical fiber end face region of a ferrule for inspection, wherein, with an autofocus facility or a zoom lens, the camera automatically changes it's field of view and re-focuses to image different sizes of fibers, fiber arrays or ferrules or to enable the detection of defects of a certain size and a processor adapted to display the imaged optical fiber end face region, wherein the processor automatically adjusts the display to accommodate the number of optical fiber end faces imaged. The system may include a cleaning module adapted to clean the optical fiber end faces, wherein the cleaning module includes a tip with a cleaning media that is moved relative to the optical fiber end faces. The processor may be further adapted to analyze the optical fiber images to determine the presence of a defect. The processor may analyze the optical fiber images by segmenting the optical fiber images to distinguish the fiber from the surrounding material of the ferrule and re-assembling the segmented fibers for display as a fiber-by-fiber view. The processor processes the fiber images in parallel to reduce the time to determine the presence of a defect. Once a threshold of defects detected has been reached, the processor may abort further inspection of the fiber or ferrule and initiates a cleaning step. The threshold for aborting inspection may be user customizable or determined by an industry standard. The system may further include a cleaning module adapted to clean the optical fiber end faces, wherein the cleaning module comprises a tip with a cleaning media that is moved relative to the optical fiber to clean the optical fiber. The ferrule may be selected from various optical fiber connectors including MT, MPO, and PRIZM or other array lens-based connectors. The cleaning module may include a force controller that controls a force pushing the cleaning tip against the optical fiber. The tip may be rotated back and forth about the long axis of the tip. The tip may be moved in an oscillatory movement that begins at one corner of an array of optical fiber end faces, crosses the array and ends at an adjacent corner of the array. The tip may be moved in a line down an array of optical fiber end faces combined with an overlaid circular cleaning path. The tip may be moved in a side-to-side motion, normal to the long axis of an MT or array ferrule, while the thread is pulled along the long axis. The tip may be removed from contact with the optical fiber end faces and repositioned before continuing with a cleaning process or repeating a cleaning process.

The system may further include a backlight facility to enable the location of a lens region of a PRIZM or other micro-lens array style connector and to enable continuity testing for optical fiber assemblies. The camera can be adapted to zoom in on individual optical fiber end faces to enable a visual inspection and evaluation. The system may further include a motion control system adapted to automatically position the camera at one or more of a ferrule and a fiber location. The processor may pre-process the image of the optical fiber end face region by one or more of removal of a known noise pattern, adaptive light leveling of image to compensate for non-uniformity of the lighting or camera response, upsampling, and contrast enhancement. The auto-focus facility may include at least one of moving a camera, moving an element in a lens or changing an optical power in a variable optical power element, or may be provided by moving an image sensor in the camera.

These and other systems, methods, objects, features, and advantages of the present invention will be apparent to those skilled in the art from the following detailed description of the preferred embodiment and the drawings.

All documents mentioned herein are hereby incorporated in their entirety by reference. References to items in the singular should be understood to include items in the plural, and vice versa, unless explicitly stated otherwise or clear from the text. Grammatical conjunctions are intended to express any and all disjunctive and conjunctive combinations of conjoined clauses, sentences, words, and the like, unless otherwise stated or clear from the context.

BRIEF DESCRIPTION OF THE FIGURES

The invention and the following detailed description of certain embodiments thereof may be understood by reference to the following figures:

FIG. 17 depicts a user interface for establishing inspection criteria;

DETAILED DESCRIPTION

The invention provides methods and systems related to enhanced fiber optic end face cleaning and inspection. To obtain high levels of transmission in fiber optic systems such as are found in communication systems and various types of fiber optic sensors, it is important that the ends of the fiber optic connections be clean and defect free when installed. Consequently, it is important to be able to clean the ends of fiber optic components including the optical fibers and to be able to inspect the ends following cleaning to verify that the ends of the fiber optics are free of defects. The invention provides an automated system and methods for rapidly and efficiently cleaning and inspecting various types of fiber optic component. The system enables automatically locating, imaging, inspecting and cleaning the surfaces of fiber ends.

Figure 1:
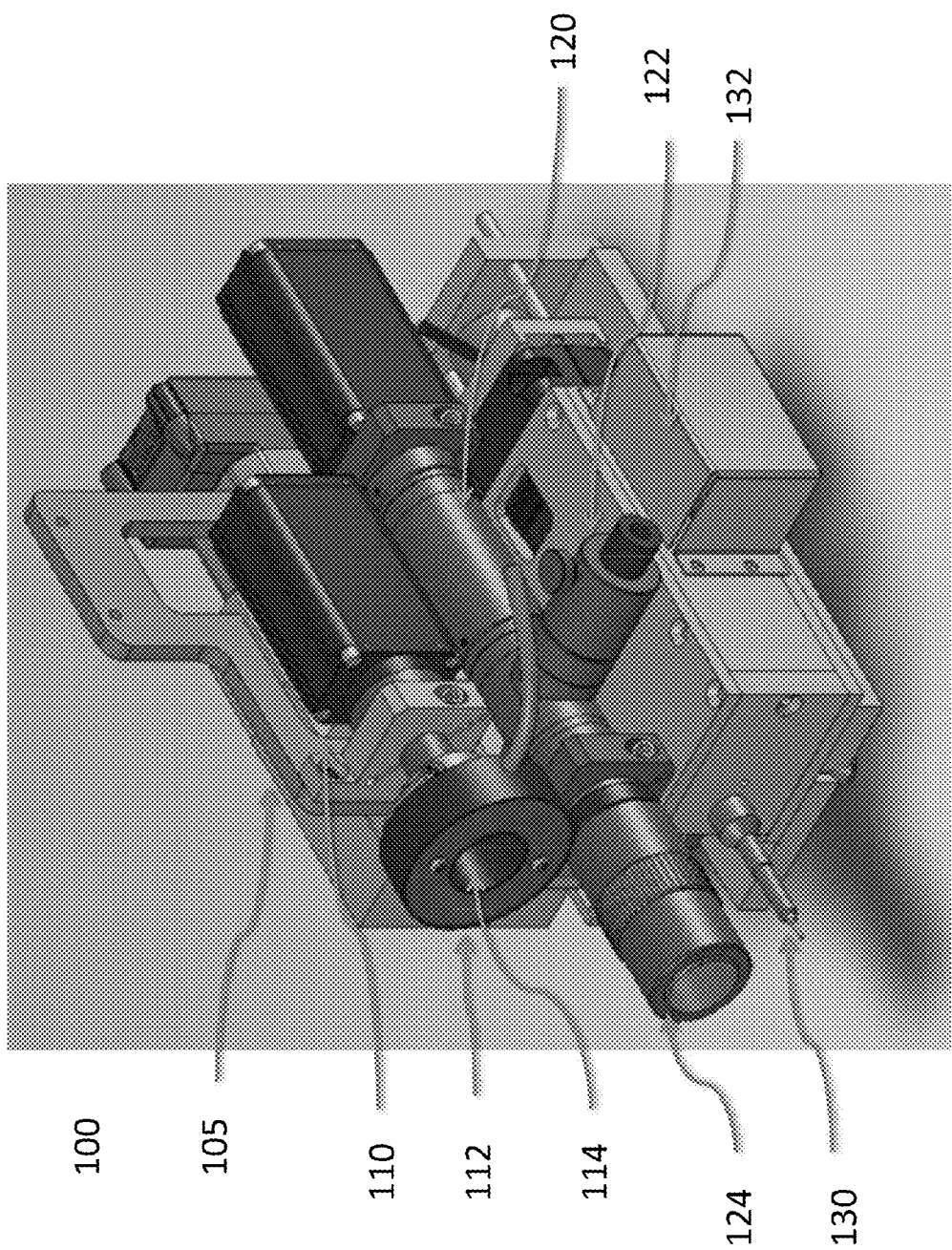
FIG. 1 is an illustration of a cleaning and inspection head assembly.

FIG. 1 is an illustration of a modular cleaning and inspection head assembly 100 in an embodiment of the invention. The head assembly 100 includes dual cameras 110 and 120 along with a cleaning module 132 and drive electronics 105. Ferrule camera 110 includes a wide FOV lens 114 and a light 112 that illuminates the wide FOV during image capture. Fiber camera 120 includes a narrow FOV lens 124 and a light 122 that illuminates the narrow FOV during image capture. The cleaning module 132 includes a cleaning tip 130. Lenses 114 and 124 can be linearly aligned with the cleaning tip 130 so that efficient movement of the cleaning and inspection head assembly from positions for image capture to cleaning is possible.

The ferrule camera 110 is used to image a fiber optic component that can include a ferrule and multiple fiber ends corresponding to at least a portion of an array of fibers in a ferrule. The image captured by the ferrule camera 110 is then analyzed to find the fiber ends and enable their respective locations to be determined. The fiber camera 120 is used to inspect the end of a single fiber at a time for defects and contamination. For example, the ferrule camera 110 can provide a FOV that is 9.4×7.2 mm in size and the fiber camera 120 can provide a FOV that is 0.2×0.2 mm in size. The cameras 110 and 120 also provide different levels of magnification and resolution. For the example given, the ferrule camera 110 provides a 0.5× magnification and captured digital images wherein each pixel corresponds to 15 microns on the ferrule. In the same example, the fiber camera 120 provides a 10× magnification and captured digital images wherein each pixel corresponds to 0.43 microns on the fiber optic. Other magnifications and resolutions are possible. These cameras are available, for example, from Basler AG, Germany. Lenses 114 or 124 can also be zoom lenses that provide adjustable magnification and field of view to enable different size fiber optics to be cleaned and inspected.

To provide for consistent focusing of the cameras 110 and 120, autofocus is provided for both cameras wherein the autofocus system includes focus adjustment and focus measurement. The focus adjustment and the focus measurement techniques for the ferrule camera 110 can be different from those used in the fiber camera 120.

Focus adjustment can be provided by various techniques as is known to those skilled in the art. Focus adjustment can be provided with focusable optics including moveable elements or variable optical power elements, such as a liquid lens or a liquid crystal lens, in lenses 114 and 124. Alternately, lenses 114 and 124 can have fixed focus and focus adjustment is provided by moving the image sensors inside the camera bodies of cameras 110 and 120 relative to the lenses. In the simplest form, cameras 110 and 120 can have fixed focus distances, and focus adjustment is provided by moving the cleaning and inspection head assembly 100 along with the cameras 110 and 120 to position the ferrule or fiber end that is being inspected at the focus distance of the respective camera being used.

Focus quality measurement to determine the focus adjustment that provides the sharpest image, can be provided by various techniques as is known by those skilled in the art. Focus quality can be determined by evaluating the relative contrast within a series of images captured with different known positions along the focus axis and selecting the focus position with the highest contrast as is done in simple digital cameras. Alternately, focus quality can be determined by a phase detection measurement on a portion of the incoming light that is diverted to a focus sensor by an inline beam splitter as is done in faster more sophisticated single lens reflex digital cameras.

To make it easier to identify fibers or to better differentiate types of debris, contaminations and scratches, cameras 110 and 120 along with their respective lights 112 and 122 can be modified. As shown in FIG. 1, lights 112 and 122 can take various forms, such as the ring lights such as shown for light 112 in FIG. 1 or axial lights with side light sources such as shown for light 122 in FIG. 1. In addition, the lights 112 or 122 can have other characteristics such as: bright field or dark field; polarized; edge light; broad spectrum; narrow spectrum. In a further embodiment, the cameras 110 and 120 along with their respective lights 112 and 122 can use different spectrums of light including: visible light, infrared light or ultraviolet light.

In a further embodiment, fiber camera 120 includes a higher resolution image sensor and the associated lens 124 has a less narrow FOV so that multiple fibers in an array can be imaged together. By capturing images of the ferrule such that multiple fibers can be inspected in each image, the number of images that need to be captured for each ferrule is reduced and as a result, the speed and efficiency of the inspection process is increased. For example, the number of pixels on the image sensor in fiber camera 120 can be increased by 4×. At the same time, the field of view of the lens 124 can be increased to image an area that is twice as wide and twice as high. As a result, the fiber camera 120 and lens 124 can be used to image a 2×2 array of fibers in each image and as a result, the time to capture images of all the fibers in the array is correspondingly reduced.

Figure 2:
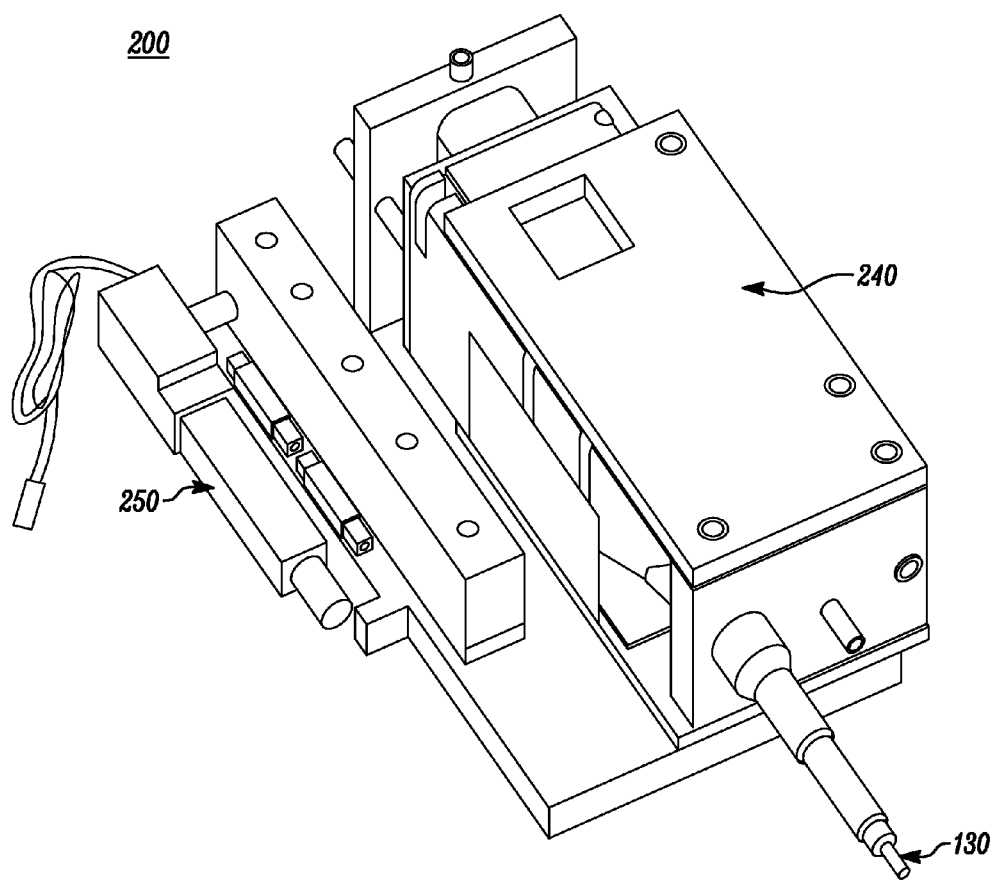
FIG. 2 is an illustration of a cleaning module assembly.

FIG. 2 is an illustration of the cleaning module assembly 200. Wherein the cleaning module assembly 200 includes a cleaning tip 130, a cleaning media controller 240 and a force controller 250. In one embodiment of the invention, a contact cleaning technique is utilized, such as that described in U.S. Pat. No. 6,758,605, which uses a thread based cleaning media however, other cleaning media are possible such as fabrics, yarns or felts. The cleaning media can be comprised of various lint-free materials including for example, polyester or nylon. The cleaning media is guided through the cleaning tip 130 so that when the cleaning tip 130 is pushed forward to contact the fiber optic, the cleaning media is pulled across the end of the fiber optic to clean the fiber optic. The tension and speed of movement of the cleaning media are controlled by the cleaning media controller 240. The force pushing the cleaning tip 130 against the fiber optic is controlled by the force controller 250.

Figure 3B:
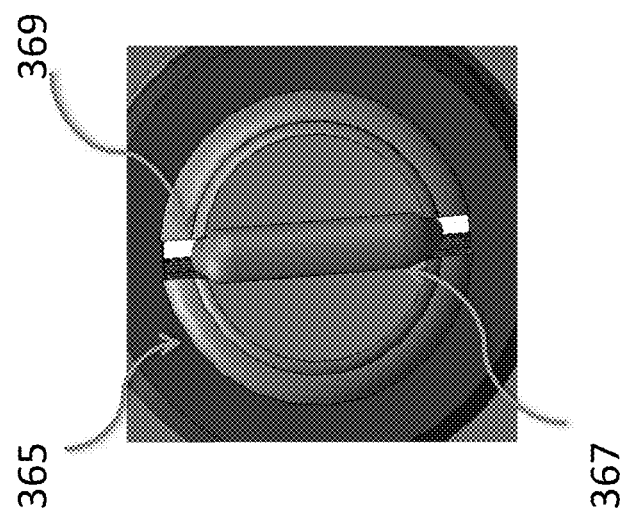
FIG. 3B is an illustration of a cleaning tip.
Figure 3A:
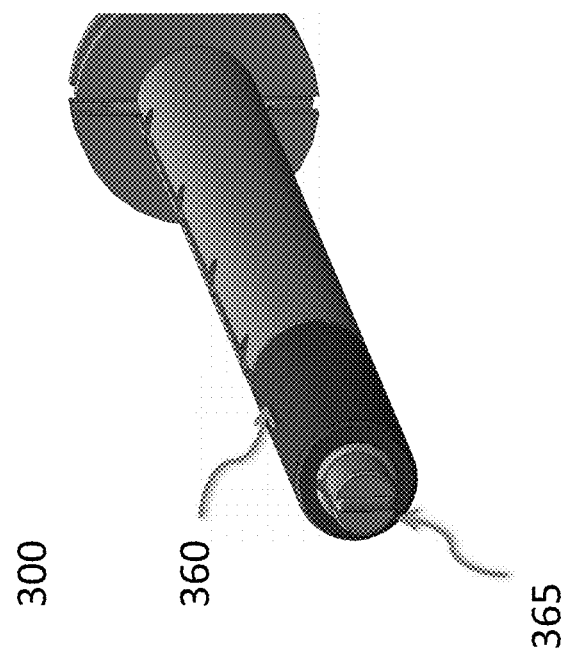
FIG. 3A is an illustration of a cleaning tip assembly.

FIG. 3A is an illustration of the cleaning tip assembly 300, which includes a cleaning tip 365 attached to a cleaning tip extension 360. A more detailed illustration of the cleaning tip 365 is shown in FIG. 3B where the cleaning media 367 is shown in a media guide slot 369. While FIGS. 3A and 3B show cleaning tip 365 as being round, other shapes such as square or rectangular are also possible to better fit the ferrule type being cleaned. During the cleaning process, the cleaning media 367 is moved by the cleaning media controller 240 from a supply roll through a media guide slot 369 to a takeup roll, where the supply roll and the takeup roll can be located inside the cleaning media controller 240. Wherein the cleaning media can be supplied on the supply roll and the takeup roll as a cartridge (not shown) that is inserted into or located adjacent to the cleaning media controller 240. The media guide slot 369 guides the cleaning media 367 down the cleaning tip extension 360 to the cleaning tip 365 such that the cleaning media 367 is partially exposed at the cleaning tip 365 during the cleaning process and contact is achieved with the fiber optic with the force provided by the force controller 250. It is the dragging of the cleaning media 367 across the end of the fiber optic and the cleaning properties of the cleaning media 367 such as the abrasiveness relative to contaminations that determine the effectiveness of the cleaning process. As shown in FIGS. 3A and 3B, the cleaning media 367 is largely protected while moving through the media guide slot 369 to reduce the chance for contamination, as such, it is only exposed at the cleaning tip 365 (e.g. 2.5 mm). By dragging the cleaning media 367 through the cleaning tip 365, new unused cleaning media 367 is continually provided while used cleaning media 367 along with particles and materials that have been removed from the end of the fiber optic from the cleaning process is continually carried away. In embodiments, the system will track the cartridge use and prompt the user when it is time to replace a cartridge. The system software will have the functionality to go to a preset location and present the cleaning system to the user to change the cartridge. In embodiments, cleaning tip extension 360 comprises a hard plastic or metal that is shorter than the plastic cleaning tip 365 so as to avoid metal contacting the optical fiber end faces.

Figure 4:
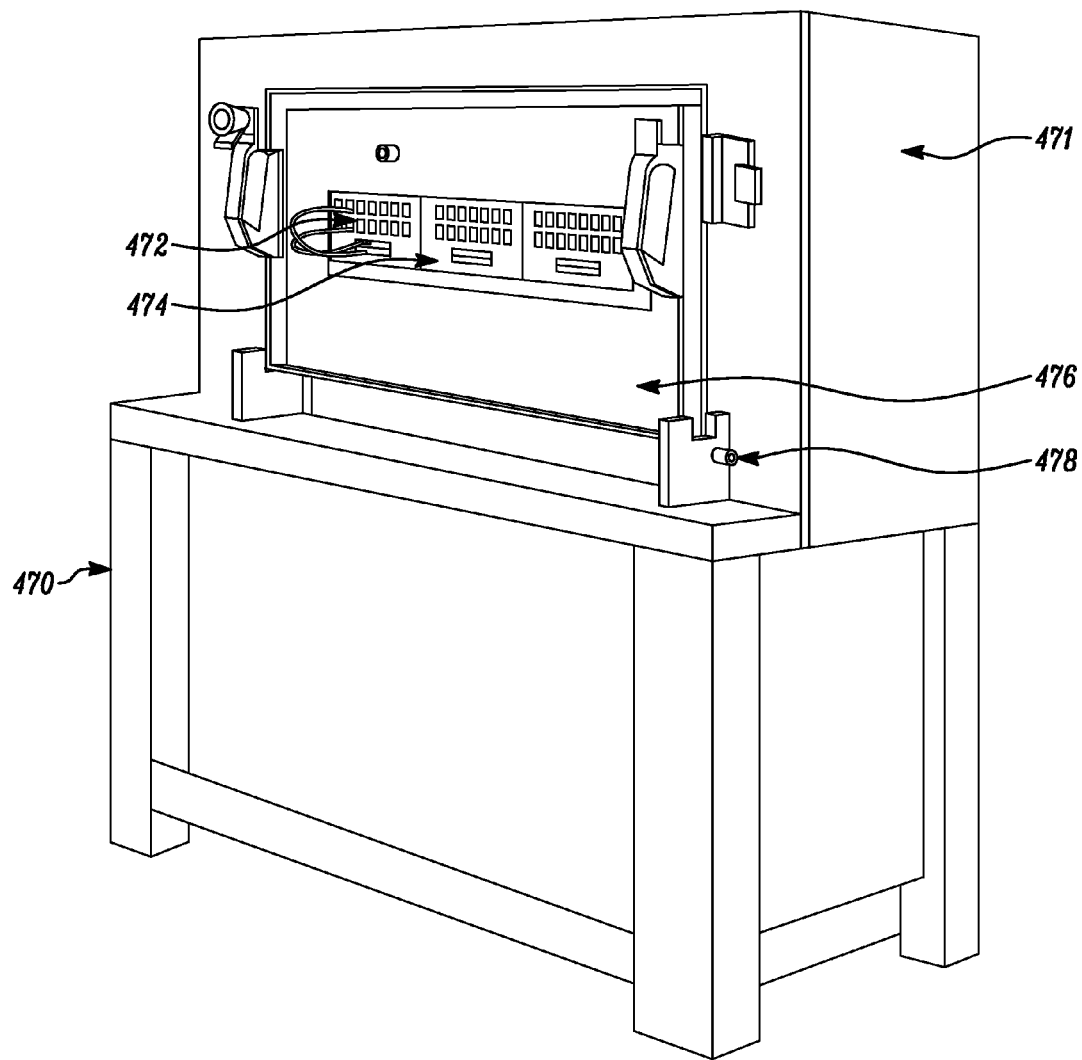
FIG. 4 is an illustration of a cleaning and inspection device.

FIG. 4 is an illustration of a cleaning and inspection device 400 that includes the cleaning and inspection head assembly 100 show in FIG. 1. The cleaning and inspection device 400 includes a case 470, a test chamber 471 and a rack mount 478. The fiber optic connectors 472 to be tested are mounted into connector test plates 474 which are affixed in a test plate rack 476. The test plate rack 476 is then loaded into the cleaning and inspection device 400 where it is held in place by the rack mounts 478. The cleaning and inspection head assembly 100 is mounted inside the test chamber 471 in the cleaning and inspection device 400 so the cleaning and inspecting are done in a controlled environment to avoid contamination of the fiber ends or ferrules. The test chamber 471 can include a filtration system with circulating air that is continuously filtered to remove any airborne debris associated with the cleaning process. The cleaning and inspection head assembly 100 is attached to a motion control system such as a translating table (not shown), which can move rapidly and accurately in directions X, Y and Z. In embodiments, the translating table includes a Y-stage. In addition, the cleaning and inspection head assembly 100 is accurately located relative to the fiber optic connectors 472 that are being cleaned and inspected. To accomplish this, a series of positive stops and tapered mounts are included for the connector test plate 474, the test plate rack 476 and the rack mount 478. In a further embodiment, the connector test plate 474 or the test plate rack 476 can have different configurations so that fiber optics and fiber optics devices with different geometries or orientations can be cleaned and inspected. In particular, it is important to be able to clean and inspect rack mounted electronics with fiber optic devices which tend to be relatively deep so that the test plate rack 476 can stick out from the front of the cleaning and inspection device 400 while using the rack mounts 478 as shown in FIG. 4. Other geometries are possible. For example, cleaning and inspection device 400 with its large inspection window, can test large boards and backplane components that are the final end products containing optical cable assemblies. It can also test larger numbers of smaller assemblies, including cables and accessories such as loopback devices. In an embodiment, the cleaning and inspection device 400 may include an external elevator with travel that extends the inspection area. For example, the range of travel may be 300 mm and inspection area may be extended to 600×535 mm. The elevator adds motion to elevate the fixture receiver. The elevator may be used to extend the vertical range of motion. The elevator may be capable of handling large, heavy parts, such as parts up to 50 pounds.

Figure 5:
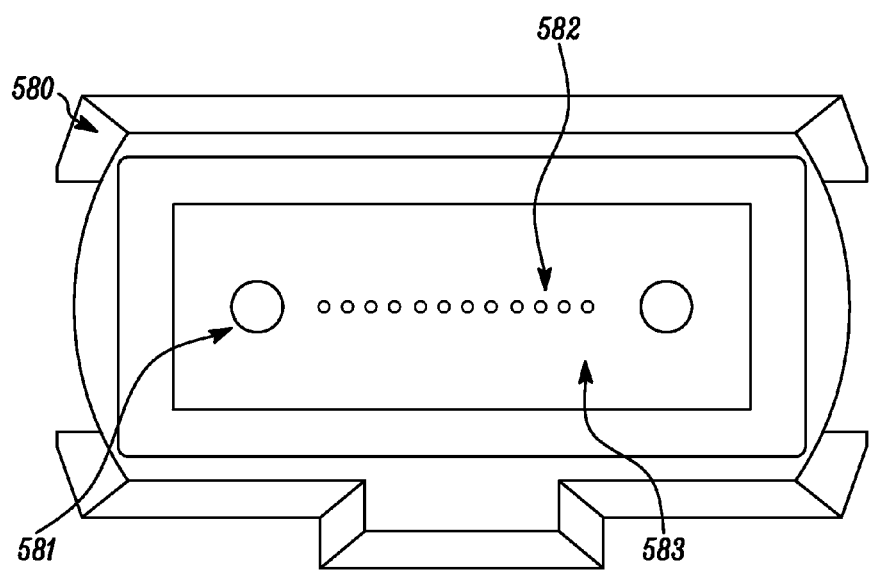
FIG. 5 is an illustration of a fiber optic connector with a linear array of fiber optics.
Figure 6:
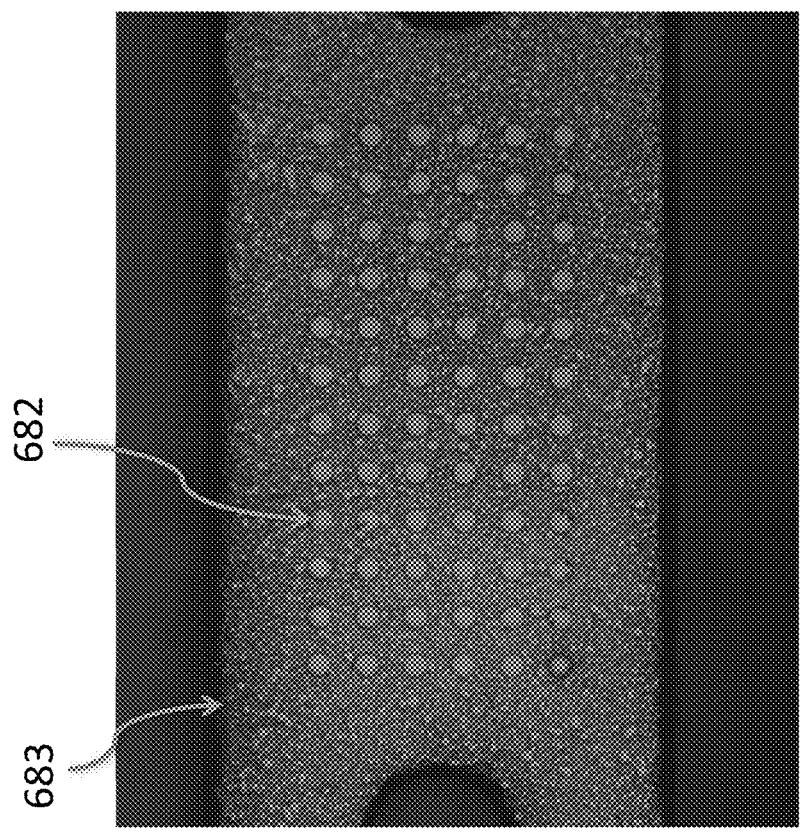
FIG. 6 is an illustration of a ferrule with a two dimensional array of fiber optics.
Figure 7:
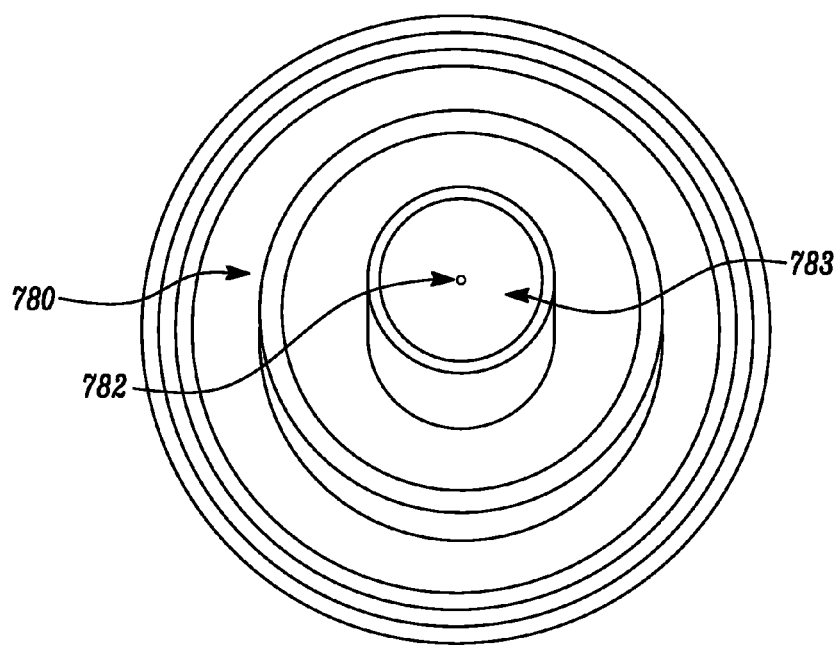
FIG. 7 is an illustration of a fiber optic connector with a single fiber optic.

The cleaning and inspection method and apparatus of the invention is meant to work with a variety of fiber optics, ferrules and fiber optic connectors, including connectors with single fiber or multi-terminal fibers. Exemplary types include cylindrical ferrules with single fibers, such as FC, SC, ST, LC, MU, SMA, and ferrules with multiple fibers such as MT, MPO, and PRIZM. In addition, multiple ferrules, also called termini, may be housed in various styles of round or rectangular connectors such as MIL-38999 circular connectors and array connectors from companies such as Molex Fiber Optics. FIG. 5 is an illustration of a fiber optic connector 580 with a linear array of fiber optics 582. Where the linear array of fiber optics 582 is mounted in an MT ferrule 583 that has alignment holes 581. The alignment holes 581 are used to help align the linear array of fiber optics 582 within the fiber optic connector 580 and to provide a fiducial mark relative to the locations of the linear array of fiber optics 582 in the ferrule 583. FIG. 6 provides an illustration of an MT ferrule 683 with a two dimensional fiber optic array 682 for comparison. FIG. 7 is an illustration of a fiber optic connector 780 with a single fiber optic 782 in a cylindrical ferrule 783. FIGS. 5, 6, and 7 are provided to show examples of the different types of fiber optic connectors that can be cleaned and inspected by the methods and apparatus provided in the present invention. In each case, the fiber optic connectors can be mounted into connector test plates 474 and affixed to a test plate rack 476 for cleaning and inspecting in the cleaning and inspecting device 400.

Figure 13A:
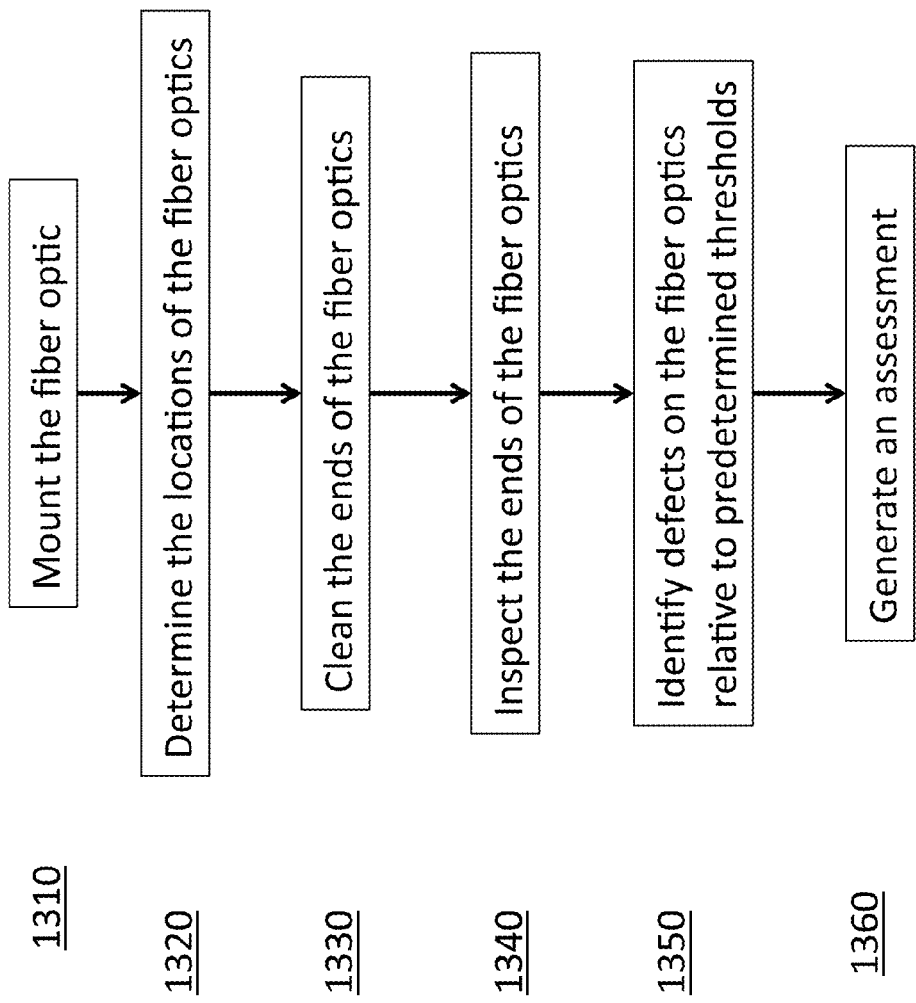
FIG. 13A is a flowchart of the automated cleaning and inspecting process.

In the cleaning and inspecting process, the cleaning and inspecting head assembly 100 is moved in X, Y and Z directions by the translating table to align the cameras 110 and 120 and the cleaning tip to the fiber optics to be cleaned and inspected. To provide a rapid and efficient cleaning and inspection process, the connector test plate 474 containing the fiber optics is fixed in place in the cleaning and inspection device 400 and the movements of the cleaning and inspection head assembly 100 are short due to the cameras 110 and 120 being in close proximity to the cleaning tip. A flow chart of the cleaning and inspecting process is shown in FIG. 13A. In step 1310, one or more ferrules (such as 583, 683 or 783) with associated fiber optics is (are) mounted in a connector test plate 474 which is then affixed to a test plate rack 476 and placed into the rack mounts 478 of the cleaning and inspection device 400. Other mounting techniques are possible so long as the fiber optics to be cleaned and inspected are affixed relative to the cleaning and inspection head assembly 100 and the associated translating table.

In step 1320, the cleaning and inspection head assembly 100 is moved by the translating table so the ferrule camera 110 is optically aligned to the ferrule to be cleaned and inspected. This initial alignment is done based on known dimensions of the connector test plate 474 and the associated mounting configuration of the ferrule in the cleaning and inspection device 400. For example, each ferrule's unique nominal XYZ location may be stored with the part configuration data. The light 112 then illuminates the ferrule to be cleaned and inspected and the ferrule camera 110 autofocuses and captures an image of the ferrule. The captured image of the ferrule can then be enhanced using digital image processing to increase the contrast in the image as is known to those skilled in the art. The captured image of the ferrule is then analyzed along with known dimensions of the ferrule, the fiber optic array and any alignment holes in the ferrule, to determine the estimated locations of the fiber ends. Where the enhancement and analysis of the image can be done in the electronics 105 or in an associated remote computer system.

In step 1330, the cleaning and inspection head assembly 100 is moved by the translating table so the cleaning tip 130 is aligned with the fiber ends in the ferrule as determined in step 1320. The cleaning module 132 is then moved so the cleaning tip 130 contacts the fiber ends to be cleaned. The force controller 250 controls the force of the cleaning tip 130 against the fiber end and the ferrule. The cleaning media controller 240 controls the movement of the media 367 as it is dragged through the media guide slot 369 and rubbing across the fiber ends. The translation table can then move the cleaning and inspection head assembly 100 such that the cleaning tip 365 is moved sequentially from fiber end to fiber end or in a continuous movement over the array of fiber optics in the ferrule. Alternatively, this motion may be provided by a motion system included in the cleaning assembly for this purpose. During the cleaning process, compressed air can be sprayed onto the ferrule can be applied as previously discussed. In a preferred embodiment, the process settings for the cleaning process such as the force, the speed, the movement of the cleaning tip 365, the cleaning time or the air spray can be changed based on the analysis of the captured image of the ferrule done in step 1320.

In step 1340, the cleaning and inspection head assembly 100 is moved by the translating table so the fiber camera 120 is optically aligned with the estimated location of one of the cleaned fiber ends in the ferrule. The light 122 illuminates the fiber end and the fiber camera 120 autofocuses on the fiber end. At this point, image analysis can be used to identify the fiber end and adjust the position of the camera slightly to center the fiber end in the image thereby improving the accuracy of the determined fiber location. An image of the fiber end is then captured. To ensure that the captured images of the fiber ends are free from motion blur, the movement of the translating table is stopped and allowed to stabilize before an image is captured. The general image quality of the image of the fiber end is then evaluated. In the event that the image of the fiber end is determined to not be suitable for defect identification due to such issues as a improper illumination, poor alignment to the fiber end, or external induced movement, the image capture is repeated, in some cases with changes to the illumination or positioning of the cameras by the system. In another embodiment of the invention, where identification of different types of defects is improved using different types of illumination, light 122 is comprised of more than one light type and multiple images of each fiber end are captured with different types of illumination. The image of the fiber end is then evaluated for defects.

In step 1350, based on the analysis of the image of the fiber end, defects are identified and sized. If multiple images of the fiber end were captured, the multiple images are analyzed and the identified defects in the multiple images are compared. The defects are then compared to predetermined thresholds for defect size, defect number, defect location or defect type (scratch, debris, contaminant, or other).

In step 1360, based on the comparison of the identified defects to the predetermined thresholds, an assessment is generated. The assessment can take various forms. The assessment can be a simple pass or fail. The assessment can include a defect map showing the types, locations, shapes or sizes of the identified defects. For the case of an array of fibers in a ferrule steps 1340 and 1350 involve the capture and analysis of images for each fiber optic in the ferrule and the assessment in step 1360 is generated for all the fiber optics in the ferrule. A pass/fail map can be then be generated that shows the locations of the fibers that pass and fibers that fail over the surface of the ferrule. In a further embodiment, if some of the fiber optics fails in the assessment a return to step 1330 is triggered for further cleaning.

In a further embodiment of the invention, following step 1330, the translating table can be used to move the cleaning and inspection head assembly 100 until the ferrule camera 110 is again optically aligned with the ferrule. The light 112 then illuminates the ferrule and an image of the cleaned ferrule is captured. The image of the cleaned ferrule is analyzed to verify the locations of the fiber ends in the ferrule. This additional step can be important when the ferrule as originally supplied in step 1310 has increased levels of contaminant present so the locations of the fiber ends are difficult to determine until after the ferrule has been cleaned. By analyzing an image of a cleaned ferrule, the accuracy of the determined locations of the fiber ends is improved.

Figure 13B:
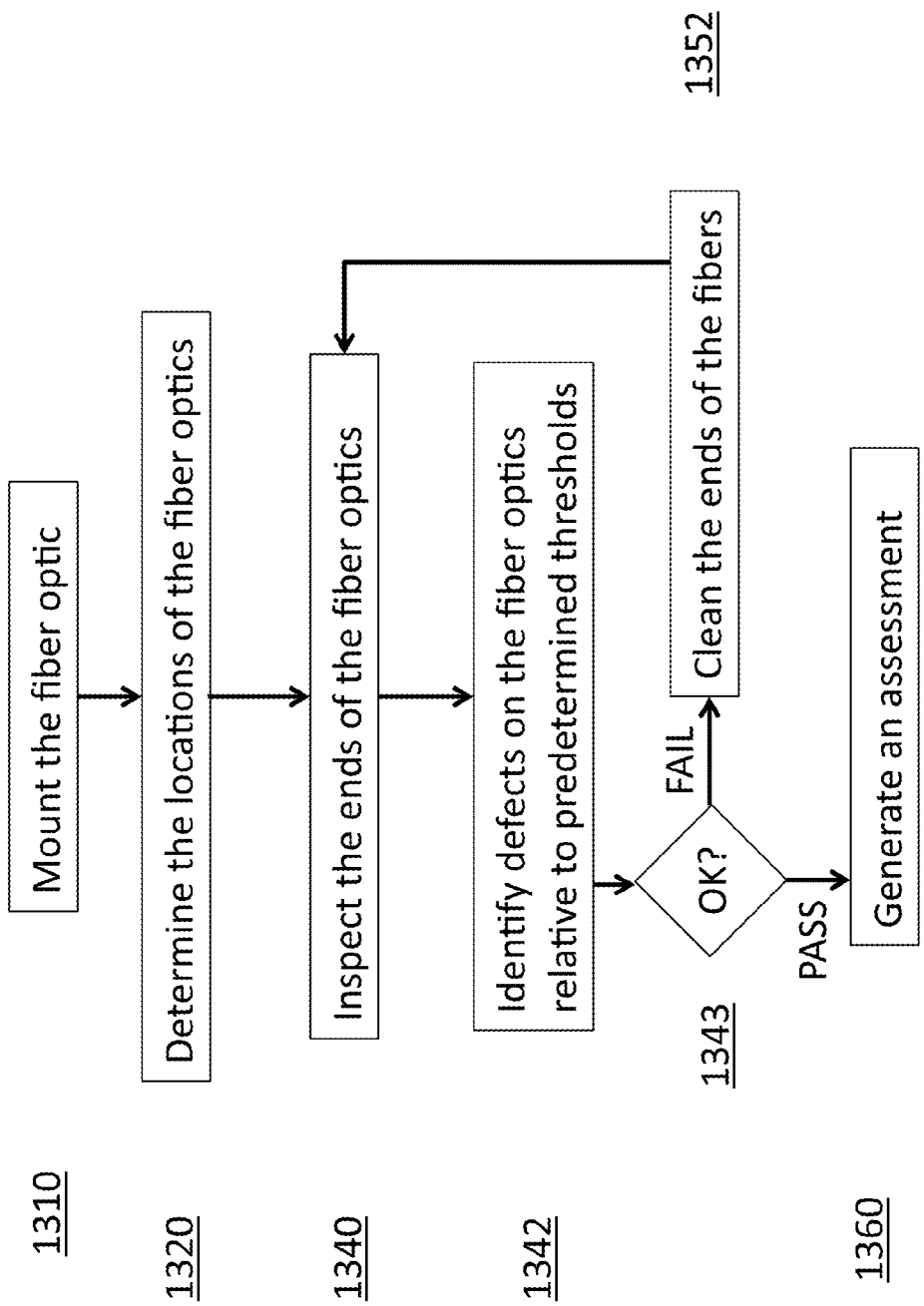
FIG. 13B is a flowchart of an automated inspection process with cleaning as needed.

In yet another embodiment, a process is provided as shown in FIG. 13B where cleaning of the fiber ends is only done when required based on the inspection. In this process, steps 1310 and 1320 are as previously described. However, following the determination of the estimated locations of the ends of the fiber optics in Step 1320 based on a captured image from the ferrule camera 110, the ends of the fiber optics are inspected as previously described for step 1340. To accomplish this, the cleaning and inspection head assembly 100 is moved from a position where the ferrule camera 110 is optically aligned with the ferrule to a position in which the fiber camera 120 is optically aligned with the first fiber to be inspected. The process then proceeds as previously described for step 1340 wherein an image of the end of the fiber is captured and analyzed. In step 1342, based on the analysis of the image of the fiber end, defects are identified and sized. If multiple images of the fiber end were captured, the multiple images are analyzed and the identified defects in the multiple images are compared. The defects are then compared to predetermined thresholds for defect size, defect number, defect location or defect type (scratch, debris, contaminant, or other). Based on this comparison, the fiber is determined to PASS or FAIL. In step 1343, if the fiber PASSES, the process continues onto step 1360 where an assessment is generated as previously described. But in step 1343, if the fiber FAILS, the process continues on to step 1352 where the ends of the fiber is cleaned and the process returns to step 1340 for re-inspection. In the case of a fiber optic array in a ferrule, steps 1340 and 1342 are continued for each fiber optic in the ferrule until either all the fibers optics have been determined to PASS or until a fiber has been determined to FAIL. When a fiber optic FAILS, the process continues to step 1352 and either the end of the fiber optic that FAILED is cleaned or all the ends of all the fiber optics in the ferrule are cleaned. Where the cleaning is accomplished as previously described for step 1330. The process then loops back to step 1340 for re-inspection.

Figure 8B:
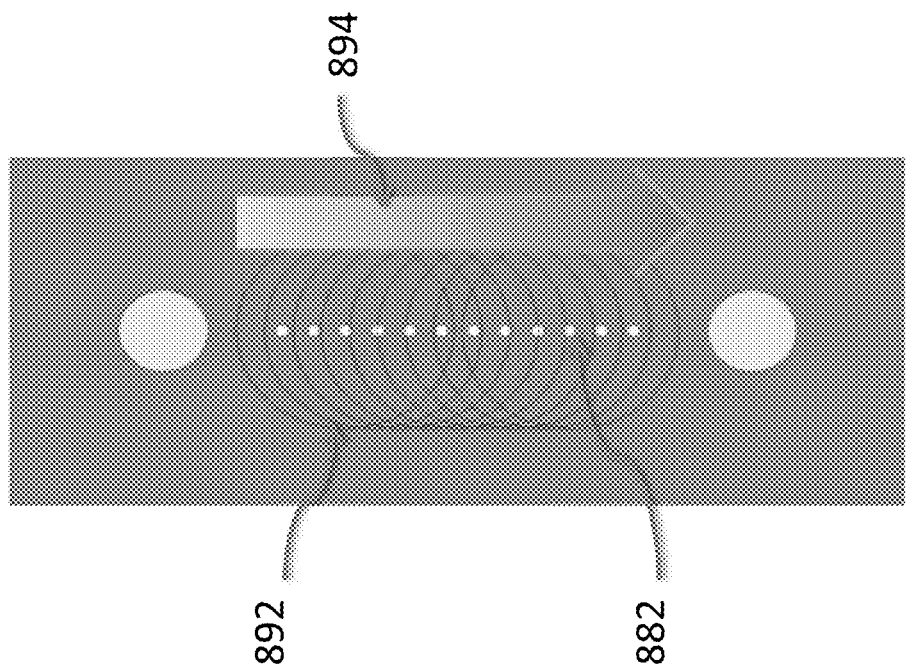
FIG. 8B is an illustration of another cleaning path followed by the cleaning tip.
Figure 8A:
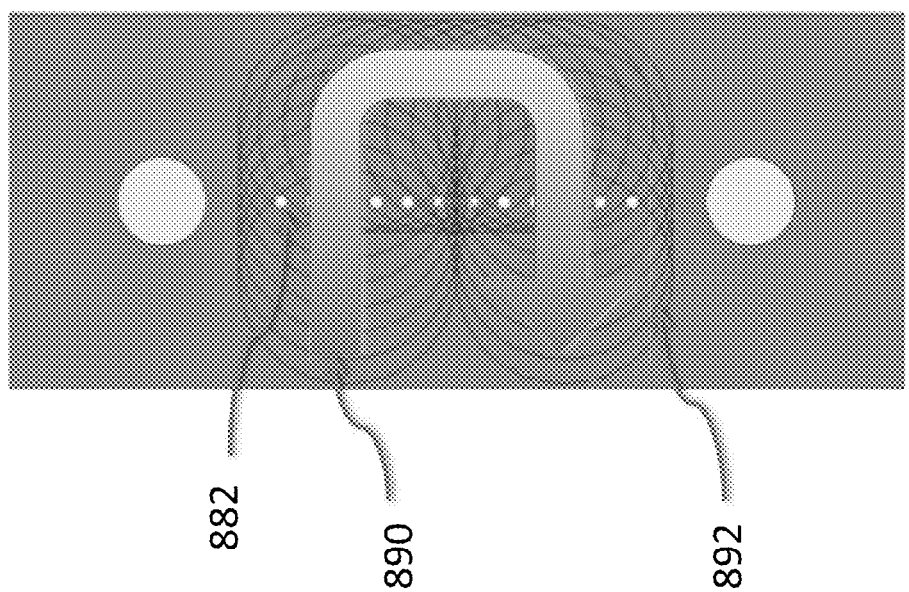
FIG. 8A is an illustration of a cleaning path followed by the cleaning tip.

FIGS. 8A and 8B provide more details on the cleaning process that is an embodiment of the invention wherein the cleaning tip 130 is moved in a complex path over a surface of a fiber optic connector. FIG. 8A is an illustration of an example of a cleaning path that can be followed by the cleaning tip during the cleaning process as it is moved over a fiber optic array 882. Wherein the cleaning path is comprised of a general cleaning path 890 that is U-shaped with an overlaid circular cleaning path 892. As such the cleaning tip 130 moves in an oscillatory movement that begins at one corner of the fiber optic array 882, crosses the fiber optic array 882 and ends at an adjacent corner of the fiber optic array 882. FIG. 8B is an illustration of another exemplary cleaning path wherein the general cleaning path 894 is a line combined with an overlaid circular cleaning path 892. Both of these cleaning paths expose the surface of the fiber optic array to multiple passes of the cleaning tip 130 to ensure that all of the optical fibers in the fiber optics array are thoroughly and efficiently cleaned. The motion of the cleaning tip 130 over the complex path can be provided by movement of the translating table as connected to the cleaning and inspection head assembly 100 or alternately, the cleaning module assembly 200 or even just the cleaning tip 130 can be moved separately by a motion control system that provides only the overlaid circular motion. In another embodiment, the cleaning tip 365 can be rotated back and forth about the long axis of the cleaning tip extension 360, so that the direction of movement of the cleaning media 367 relative to the fiber optic oscillates. In a further embodiment, the force controller 250 can vary the force applied to the cleaning tip 130 during the cleaning process or in combination with the cleaning path. By organizing the cleaning path relative to the layout of the fiber optic array in the ferrule and making it so that a single cleaning path can clean all of the fiber optics in the array, the time required for cleaning is reduced. In yet another embodiment, the cleaning process can be comprised of more than one touchdown wherein the cleaning tip is removed from contact with the fiber ends and repositioned before continuing with the cleaning process or repeating the cleaning process.

Figure 9B:
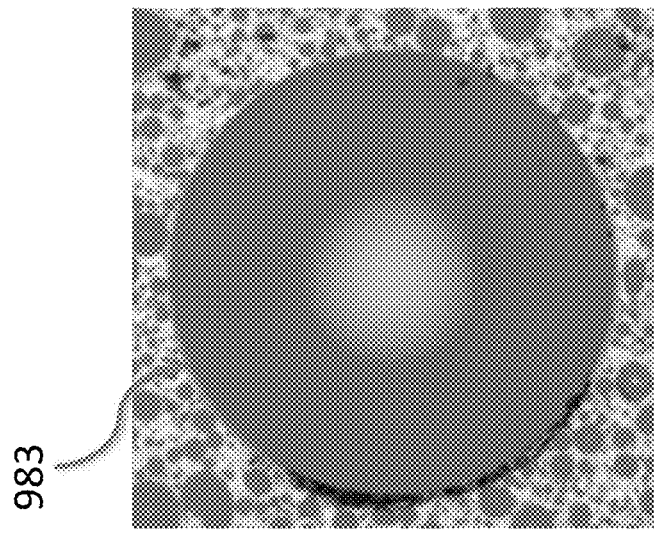
FIG. 9B is an illustration of an end of a fiber optic after cleaning.
Figure 9A:
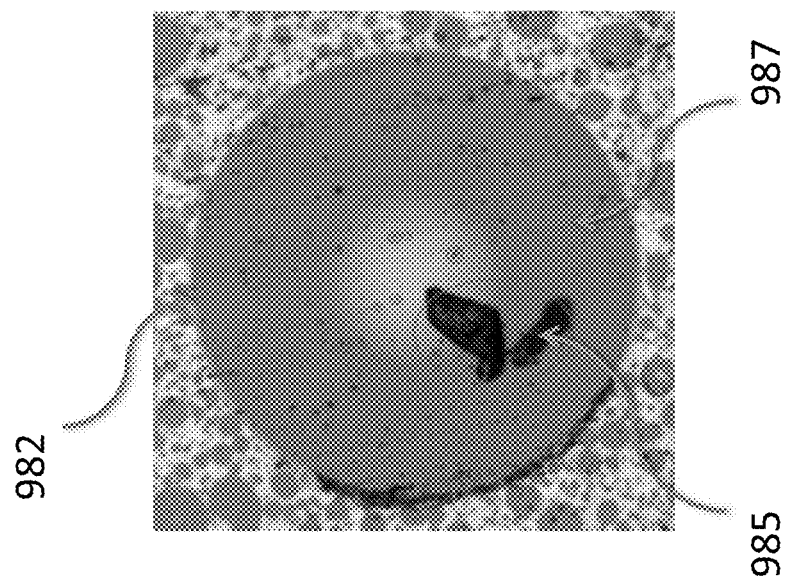
FIG. 9A is an illustration of an end of a fiber optic with debris and contamination prior to cleaning.

FIGS. 9A and 9B show example defect maps for a dirty fiber optic 982 and a cleaned fiber optic 983. Debris 985 is shown with a large circle surrounding it in the defect map, while spots 987 are shown with small circles around each spot. The clean fiber optic 983 has zero defects identified.

Figures 10A, 10B, 10C:
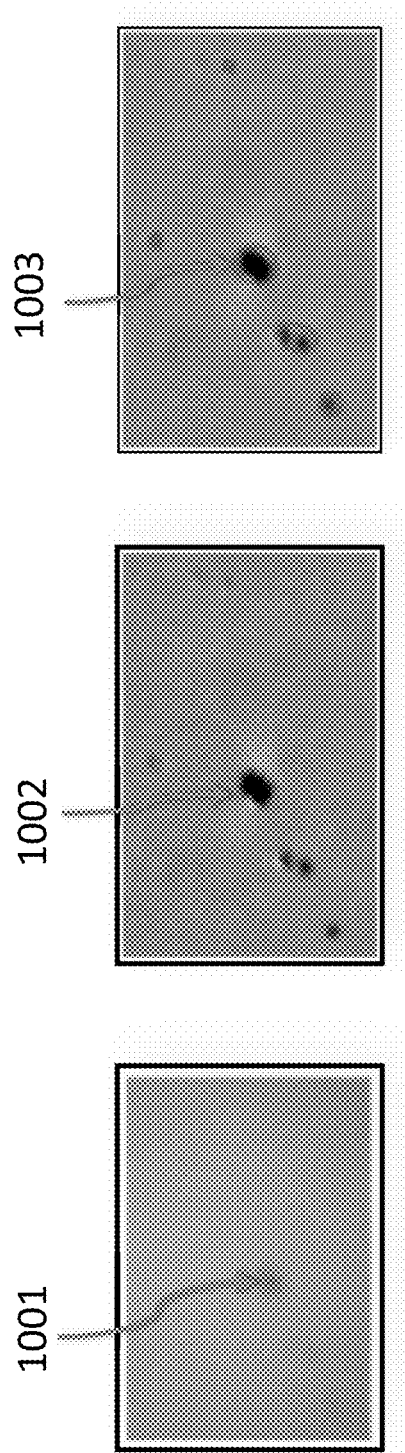
FIG. 10A is an illustration of an image of a portion of a fiber optic showing defects as originally captured.
FIG. 10B is an illustration of the image from FIG. 10A that has been enhanced to make the defects more visible.
FIG. 10C is an illustration of the image from FIG. 10B wherein the defects have been identified.

FIGS. 10A, 10B and 10C show the effect of digital image enhancement on the identification of defects. FIG. 10A shows an image of some defects 1001 on a fiber end as captured. The defects 1001 appear as faint shadows and are easily missed in a visual inspection of the image. FIG. 10B shows the same image as shown in FIG. 10A after the image has been digitally enhanced to increase the contrast. The defects 1002 are now much easier to identify, either by automated software or human inspectors. FIG. 10C shows the defects 1003 in a defect map wherein the defects 1003 are circled.

Figure 11:
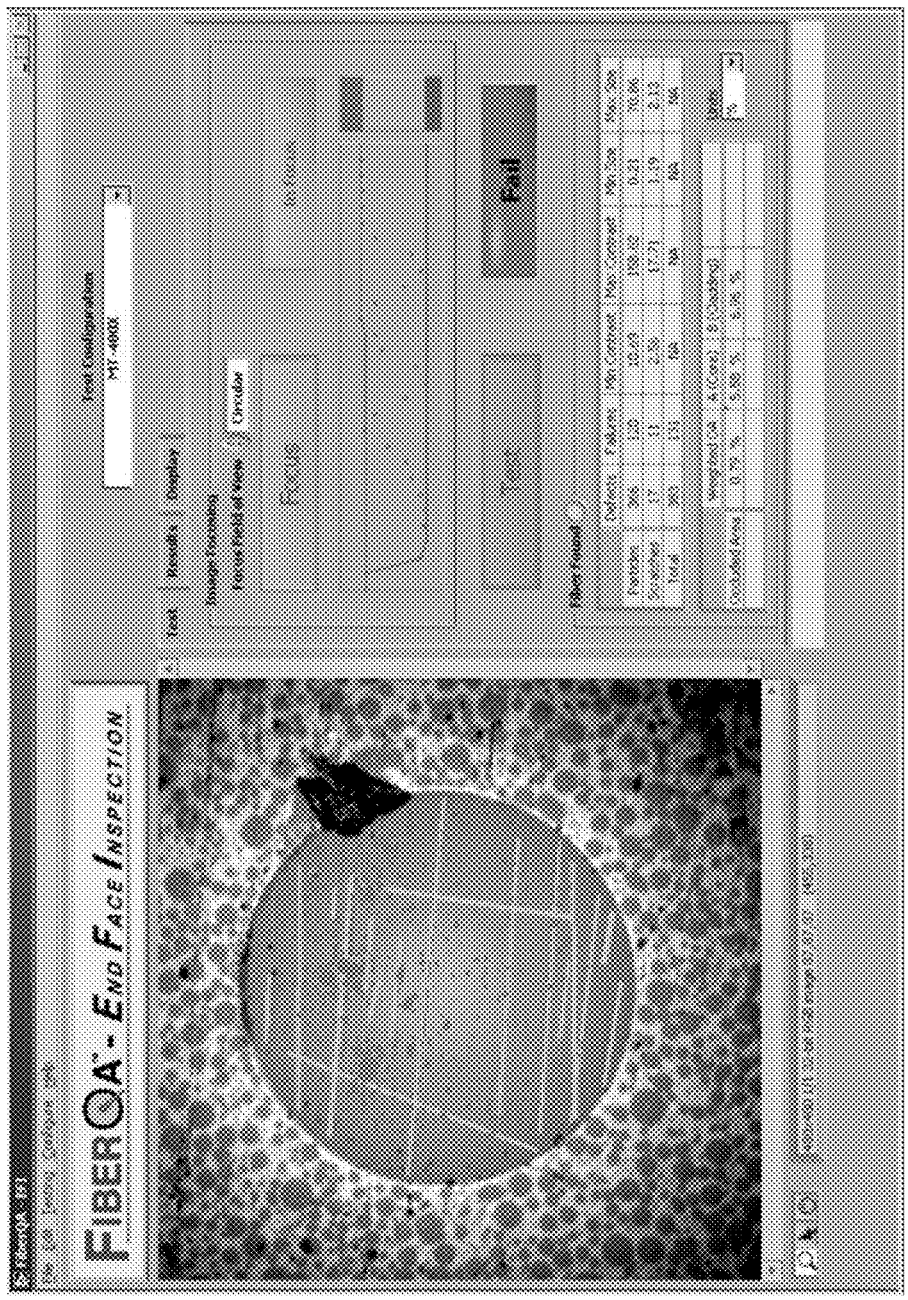
FIG. 11 is an illustration of an automated report on the defects identified on a single fiber optic end.

FIG. 11 shows an example of a generated assessment of a fiber end from the process of FIG. 13. The assessment in this case is a report that contains a variety of information including a defect map, a focus assessment, a defect characterization chart and a determination of the area occluded by the combined defects. Wherein the occluded area of the defects can be used to predict the losses associated with junctions between fiber optics such as the insertion loss or the return loss. The defect map indicates scratches and particles in their respective locations on the fiber end. A pass/fail indication is provided relative to predetermined thresholds for the scratch and particle defects found on this fiber end.

In an embodiment, the status of the ferrule may be decided on the basis of pass-fail criteria based on automated image processing of the fiber camera and ferrule camera images. The pass-fail criteria may comprise a common industry standard or custom criteria set at the user interface. The particular ferrule may then be classified as pass or fail.

In another embodiment there may be an ability to initiate cleaning of specific ferrules or fibers based on their pass-fail status. This may be followed by another image capture 1404 and image processing 1408 cycle. Improvements in yield following the cleaning may be calculated.

In addition to the inspections performed to identify defects such as debris and contamination on the ends of the fibers, the connector test plate 474 can include LED light sources and associated connections (see FIG. 4) so that the continuity of the fiber optics can be verified. In this case, an LED light is connected to a fiber optic and used to provide light into one end of the fiber optic. The ferrule camera 110 is then used to verify light coming out of the other end of the fiber optic. Multiple LEDs can be used in this way along with the ferrule camera 110 to verify the continuity of multiple fiber optics simultaneously. Alternately, a single LED can be optically connected through a backlight to provide light into multiple fiber optics simultaneously. In this way, an array of fiber optics can be tested for continuity in a simple and fast test.

Figure 12:
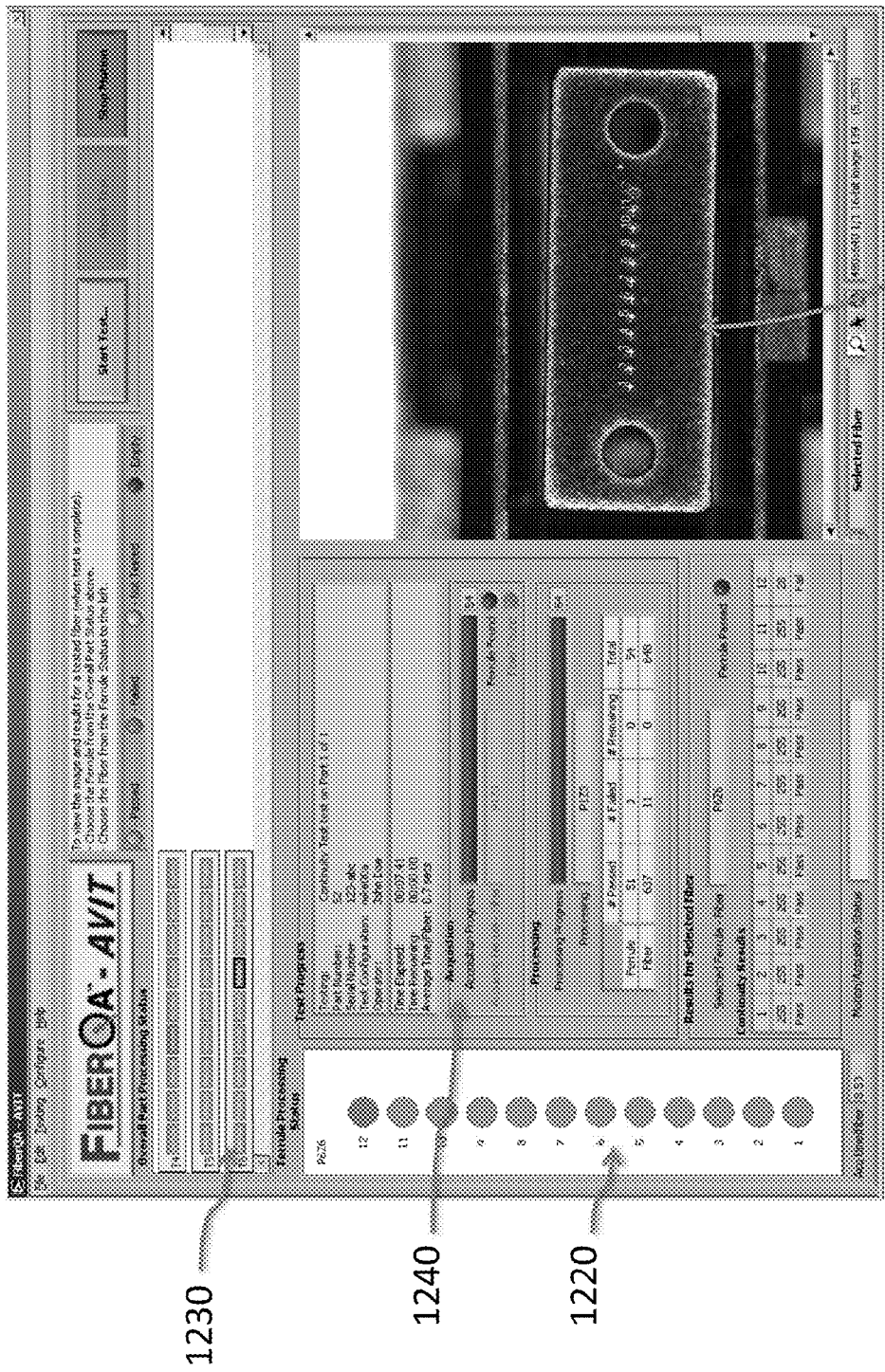
FIG. 12 is an illustration of a user interface for an automated continuity test of a part having multiple ferrules.

FIG. 12 shows an example of an automated pass/fail report page for a fiber array in a ferrule during a continuity test. An image of the ferrule 1210 being tested is shown for reference. A diagram of the ferrule 1220 being inspected is provided that shows the fiber array wherein the individual fibers that passed/failed continuity are indicated by color such as green for pass and red for fail. Colored indications of pass/fail for the individual fibers are also provided on the image of the ferrule 1210 for reference. The tested results for the entire part 1230 is shown as well, where the part is comprised of multiple ferrules. Information related to the progress of the current test is shown in a table 1240. As an example, in the diagram 1220, fiber #12 is shown to have failed the continuity test. Data related to the failure of fiber #12 is shown in table 1240 in the section labeled Continuity Results where fiber #12 has a much lower continuity measured value than the other fibers in the array.

Figure 14:
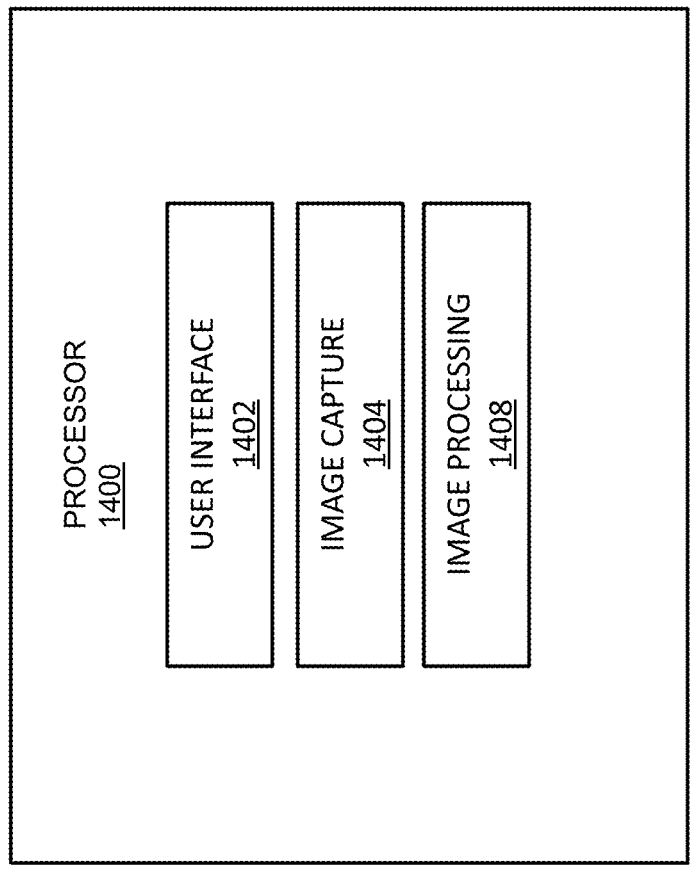
FIG. 14 depicts a processor.

In an aspect, methods and systems related to enhanced fiber optic inspection and cleaning methods are described. Disclosed herein is a system for optical fiber end face inspection further comprising a processor 1400 wherein the processor may include a user interface 1402, image acquisition 1404, image processing 1408, and the like as shown in FIG. 14.

Figure 15:
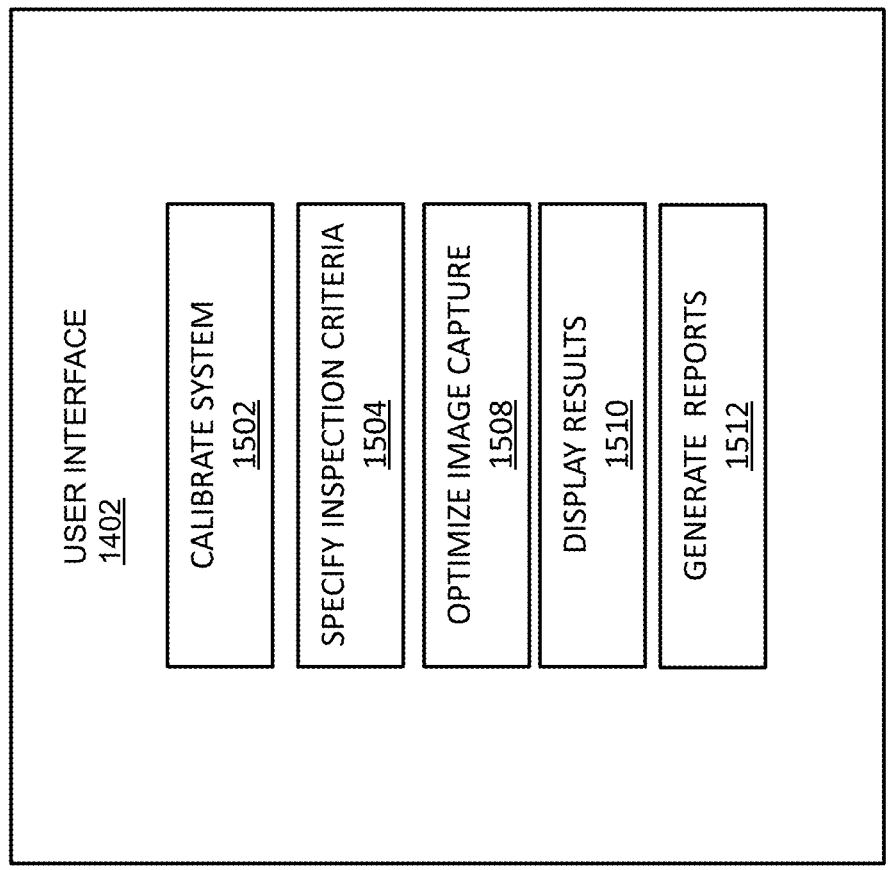
FIG. 15 depicts a user interface.

Also disclosed herein is a system for optical end face inspection wherein the user interface 1402 may include one or more of the following capabilities: calibrate system 1502, specify inspection criteria 1504, optimize image capture 1508, display results 1510, generate reports 1512, and the like. The user interface 1402 may also include detailed instruction screens for aspects of the equipment including hardware, positioning of fibers, user interface functionality, and the like as shown in FIG. 15. Functions encompassed by the user interface 1402 may be associated with different levels of security. Access to the different security levels may be protected by passwords or other known security schemes.

Calibration of the system can improve the accuracy associated with the size determination of identified defects. The step of calibrate system 1502 may include calculating the resolution available in images captured by the cameras given the current system configuration. This may involve specifying the size of a reference fiber, acquiring an image from the ferrule camera 110, the fiber camera 112 or both. The system may then segment fibers 1804 and calculate the resolution of the acquired image as a function of the size of fiber relative to the number of pixels in the segmented fiber. In another embodiment, the calibration may be entered manually. Calibrate system 1502 may also include the ability to specify positions of key fibers, ferrules, indicia and the like. Alternatively, calibration targets of various types, including linear scales or grids of dots may be imaged by the ferrule or fiber cameras and image processing applied to calculate the camera resolution.

Figure 17:
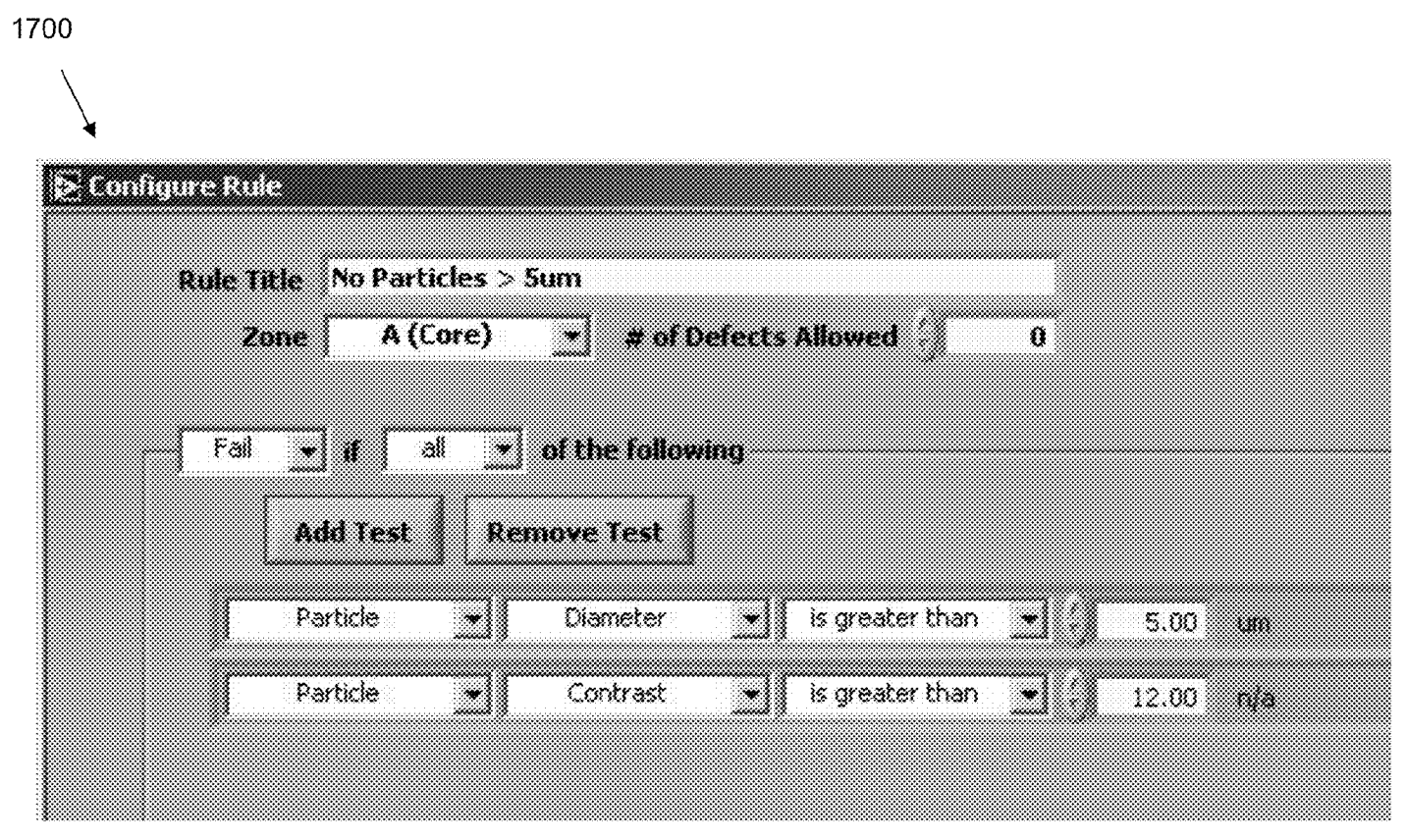

FIG. 17 illustrates an example of a user interface 1700 of the step to specify inspection criteria 1504 which may include the ability to specify industry standards regarding defect analysis criteria or specify user defined criteria to detect defects 1808. User defined criteria for detect defects 1808 may include identifying ranges and/or levels related to one or more of the following: defect size, type, location, total or percent occluded area, contrast, and the like. The user may also specify pass/fail criteria for fibers or ferrules by setting ranges or levels related to one or more of the following: number of defects, total occluded area and the like. There may be multiple user interfaces for specifying pass/fail criteria.

In a further embodiment, a single image of an entire fiber array is captured and analyzed for defects. Wherein the single image is captured with a camera and lens combination that provides sufficient resolution of each fiber in the fiber array to detect defects (such as micron scale defects) that meet relevant industry standards such as IEC 61300-3-35 or IPC8497-1 or a user established defect thresholds. Where a higher resolution camera and lens can be provided by a camera that has an image sensor with more pixels and the lens has a higher modulation transfer function (MTF). In addition, the camera and lens must have a large enough field of view to image the entire fiber array in a single image. Alternately, a camera and lens with a smaller field of view and higher resolution, can be used, however in this case, a series of adjacent images are captured such that all the fibers in the fiber array are imaged in multiple rather than a single image. The advantage of these two approaches is that the number of images captured is greatly reduced compared to the approach, previously described, wherein images are captured for each individual fiber in the fiber array, to just one or a few images. For example for the fiber array shown in FIG. 6, with the previous approach 72 images are captured, while with this approach only one or two images are captured (see FIG. 21). As a result, the time required to image the fiber array is drastically reduced, wherein each image captured requires time for alignment, autofocus, exposure, and inter-frame image averaging as parts of the image capture process.

Figure 19:
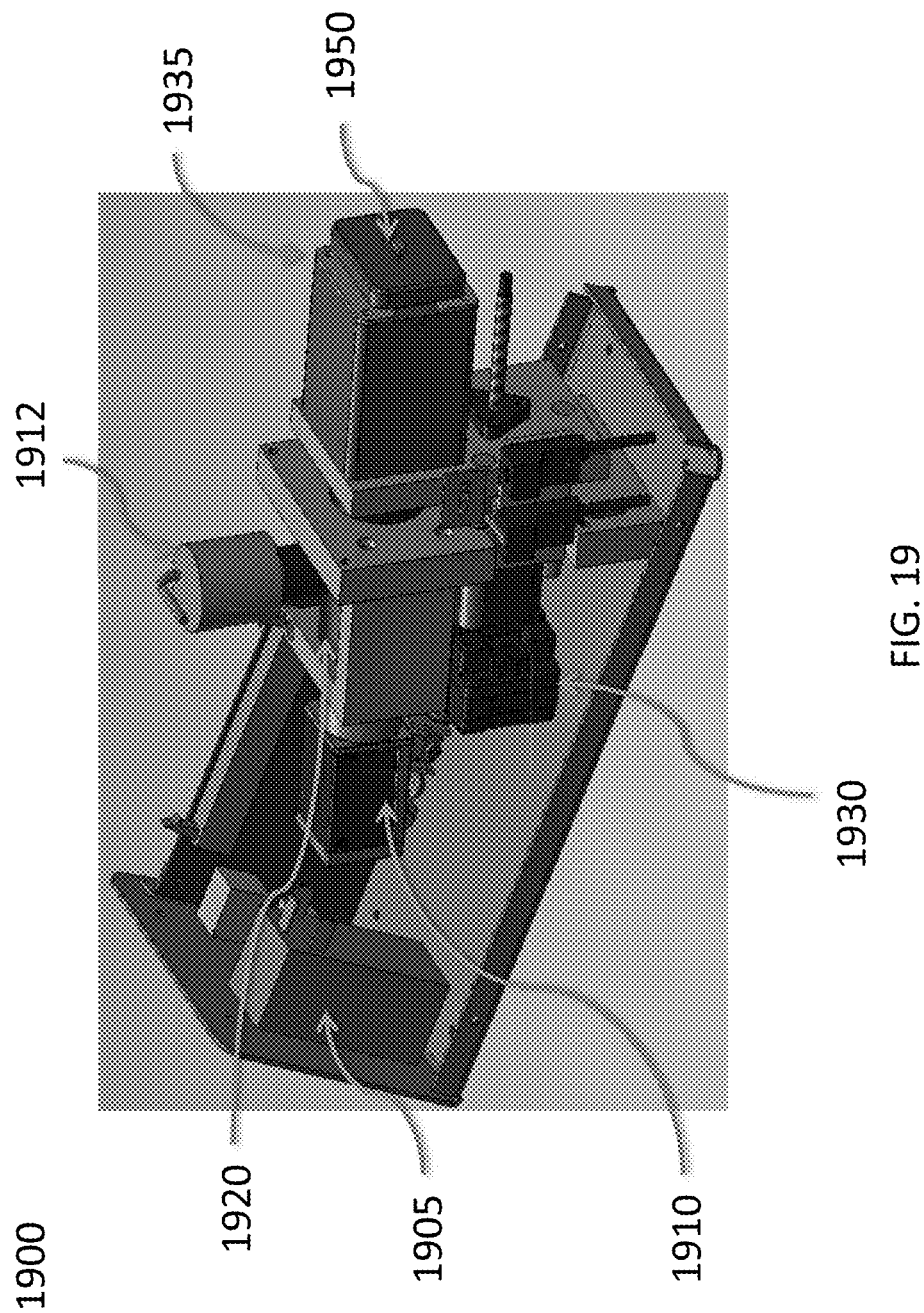
FIG. 19 is an illustration of a single camera inspection device assembly for inspecting ferrules.
Figure 20:
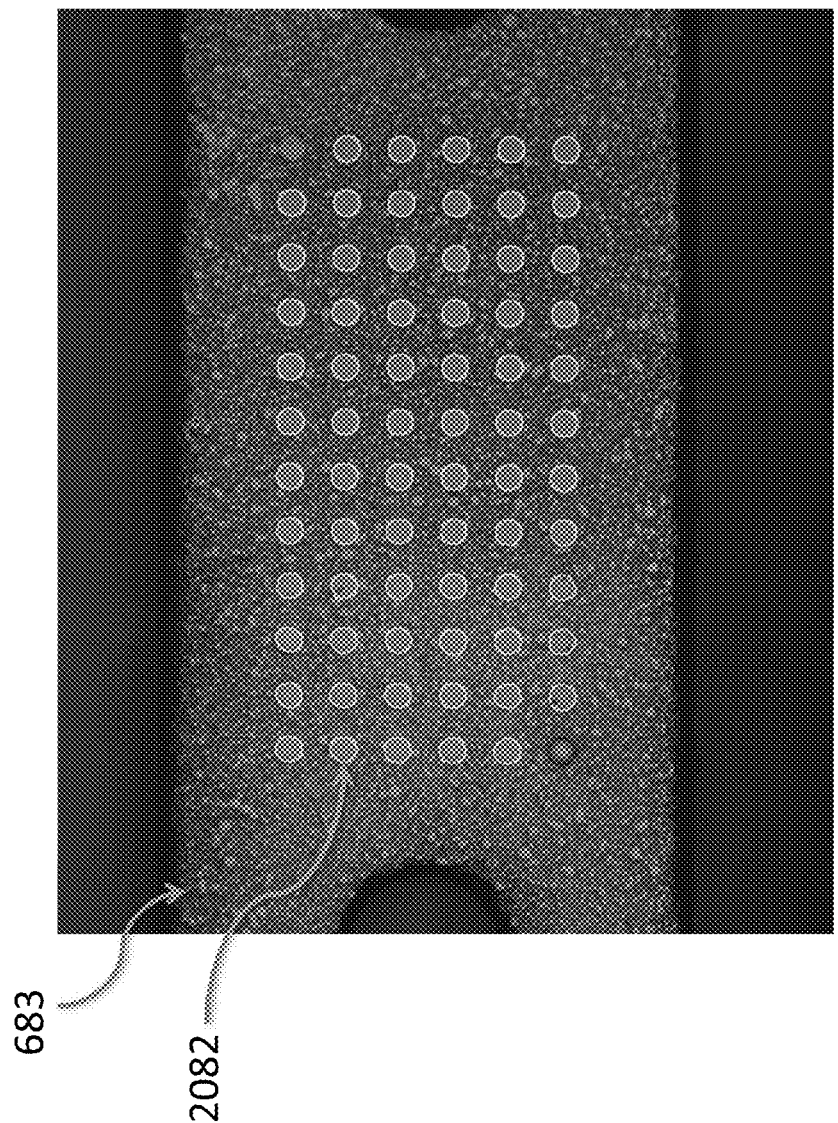
FIG. 20 is an illustration of an image of a ferrule with identified fibers circled.

FIG. 19 shows an illustration of a single camera inspection device assembly 1900 that includes: electronics 1905, a camera 1910, a light 1912, a lens 1920, a motion control system 1930 and a fixture 1935. A fiber optic part 1950 such as an MT ferrule, is inserted into the fixture 1935 to enable the polished surfaces of the fiber optic part 1950, including the ends of the fibers and the ferrule surface, to be imaged by the camera 1910 and lens 1920. The camera 1910 and the lens 1920 capture high-resolution images of the entire fiber array on the ferrule. For example, FIG. 6 is an illustration of a captured image of a ferrule 683 with a fiber optic array 682 that contains 72 fibers. In this embodiment of the invention, the resolution of the single captured image shown in FIG. 6 is sufficiently high that defects can be identified in the individual fibers. After capture, the image of ferrule 683 is then analyzed to identify the locations of the fibers in the fiber array. FIG. 20 is an illustration of an image of a ferrule wherein the identified fibers 2082 have been circled.

Figure 21:
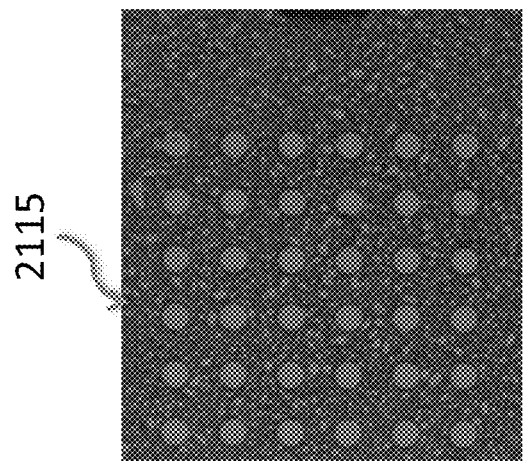
FIG. 21 is an illustration of two subimages of a ferrule as captured.
Figure 21:
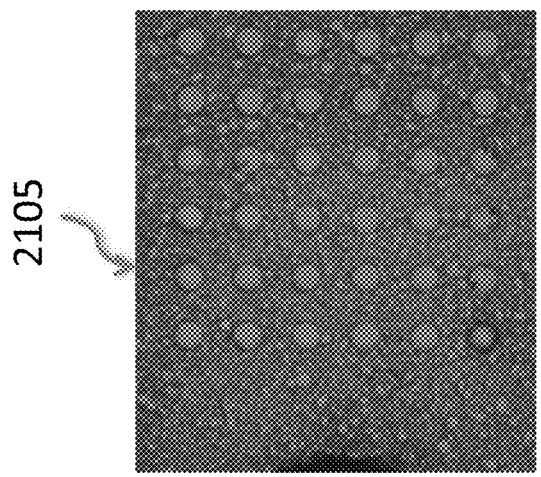

In the event that the camera 1910 and lens 1920 have sufficient resolution to detect the desired size of defects, but doesn't have a large enough field of view to image the entire fiber array, multiple adjacent sub-images are captured so that the entire fiber array is imaged. FIG. 21 shows an illustration of two sub-images 2105 and 2115 that have been captured from adjacent areas left and right respective areas of the fiber optic array 682. As such, the sub-images 2105 and 2115 each include 36 fibers and together they image the entire fiber optic array 682 comprised of 72 fibers. In this case, the camera 1910 must be repositioned and possibly refocused between capturing the two sub-images 2105 and 2115. Where the positioning of the camera 1910 for the capture of each sub-image is done by the motion control system 1930 and the positioning is based on the known dimensions of the ferrule 683 and associated fiber array 682. Further adjustment of the camera position can be done based on automated analysis of images captured prior to the capture of the sub-images 2105 and 2115.

Figure 22:
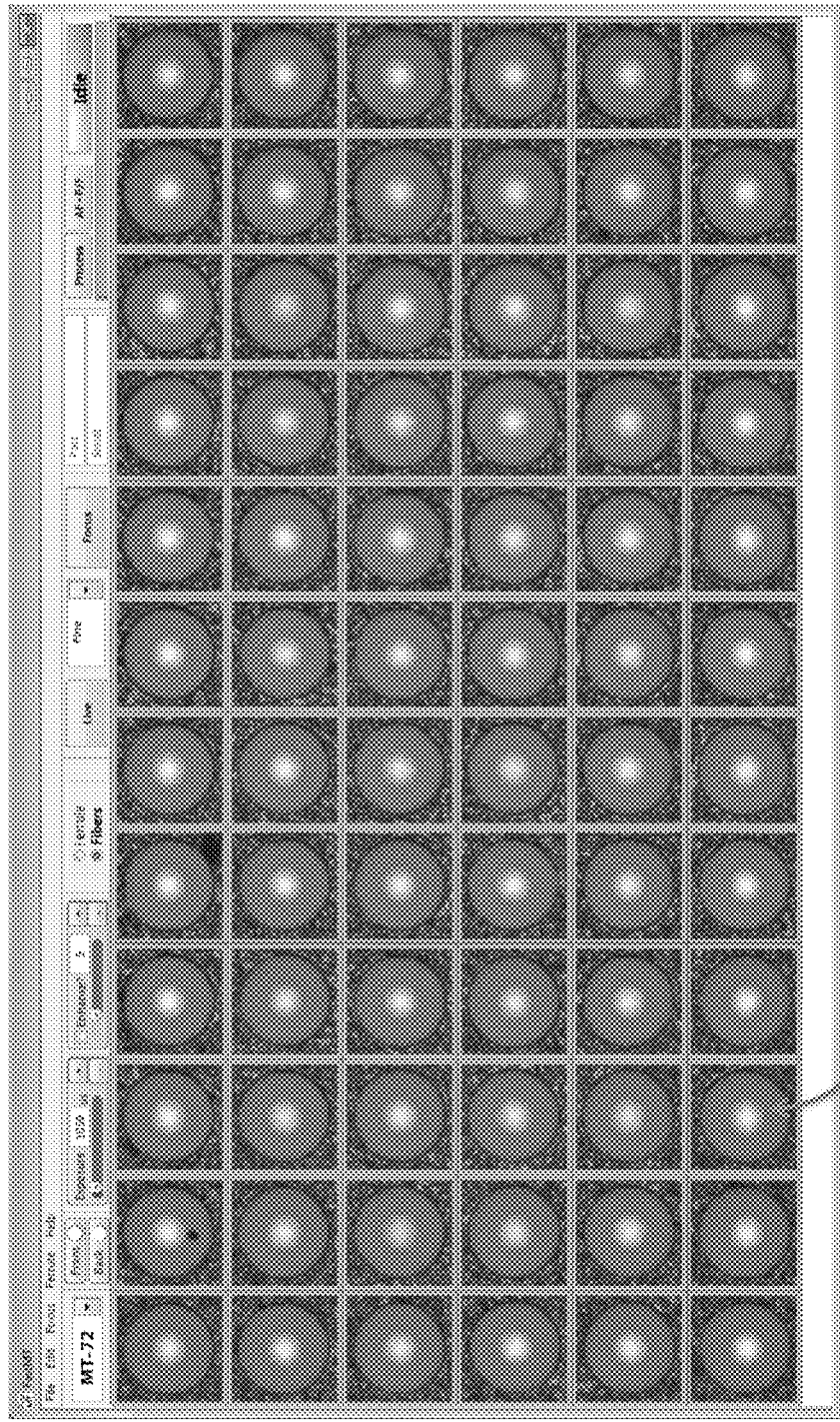
FIG. 22 is an illustration of a segmented image of a ferrule that shows all the cropped images of the fibers in the array.
Figure 23:
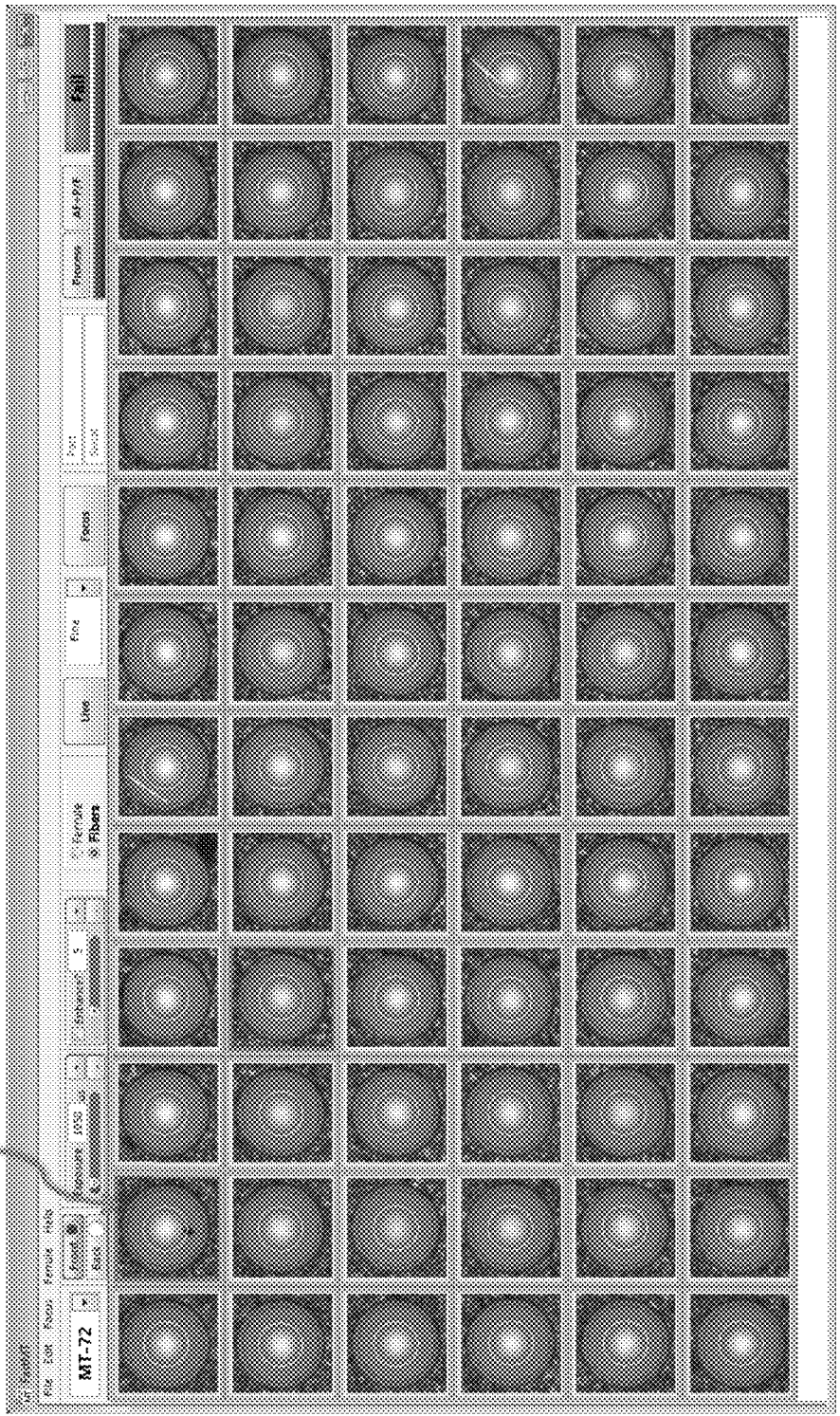
FIG. 23 is an illustration of a segmented image of a ferrule showing the results of inspection for defects.

After the fibers in the fiber array 682 have been identified as shown in FIG. 20, cropped sub-images 2225 of each fiber are prepared and a segmented image 2220 is prepared with cropped images as shown in FIG. 22. Each of the cropped sub-images 2225 of the individual fibers is then inspected to identify defects. Following the inspection of each cropped sub-image, the fibers are determined to pass or fail and an inspection report 2330 is generated that shows the cropped sub-images of the individual fibers with a colored box to show which fibers passed and which failed. As shown in the inspection report 2330 of FIG. 23, two fibers were found to have defects and these were outlined with a red box. For example, a defect in the fiber sub-image 2335 can be seen to contain a relatively large particle.

This method of displaying the defect inspection information for the individual fibers in a defect report containing a condensed array of sub-images (see FIG. 23), can make it easier to assess the results of the inspection process when many fibers are included or many fiber optic parts are included. The defect report can include one or more of the following: an indication of the pass-fail status of the individual fibers (see FIG. 16), an indication of the pass-fail status of the ferrule. The display of one or more fibers on a single screen can include the ability to select and display more detail on an individual fiber (see FIG. 16) which may include a higher resolution image of the fiber face, a more detailed defect map, additional information on the defects, and the like.

Figure 24:
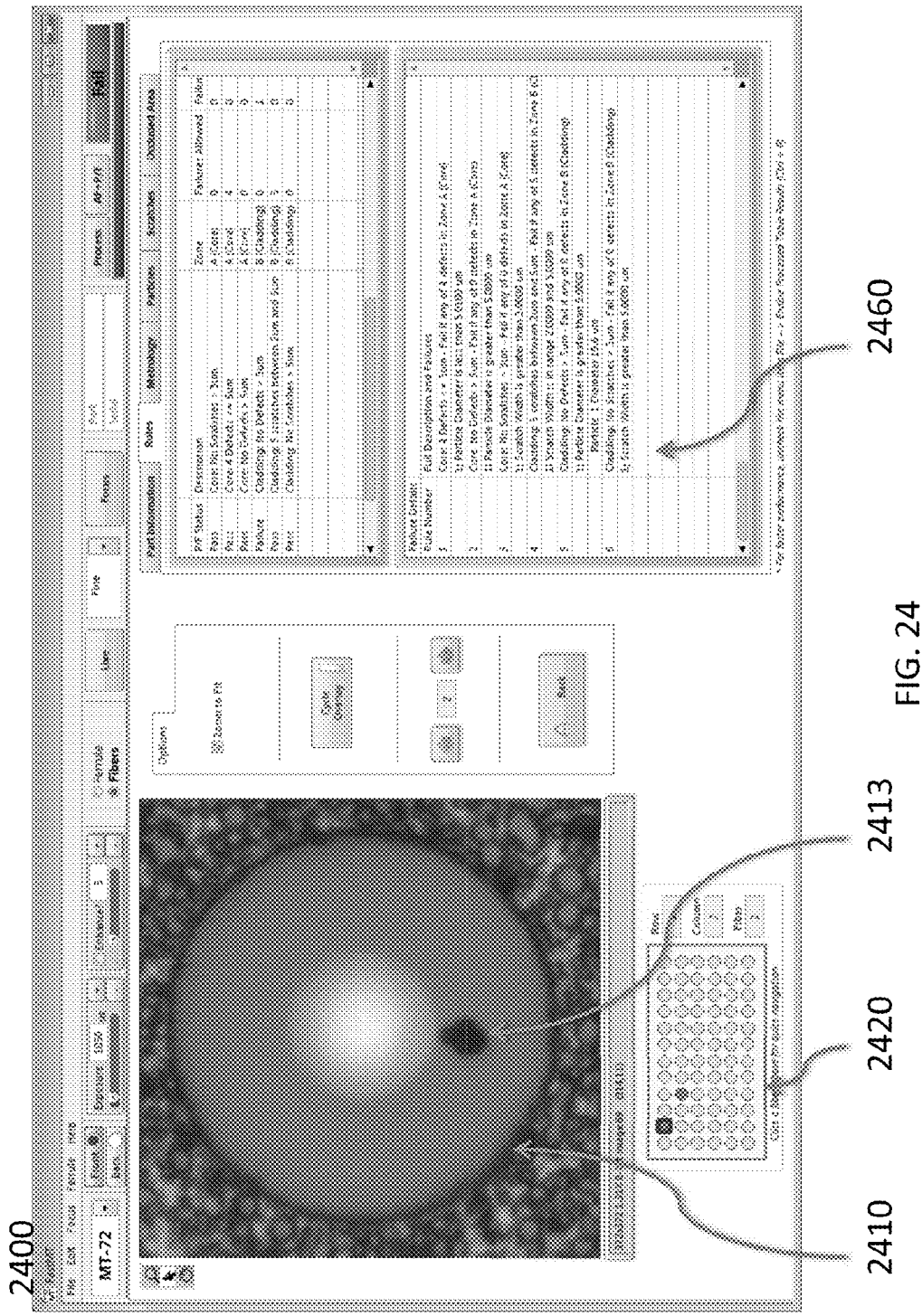
FIG. 24 is an illustration of an automated defect report for a fiber with the image as captured.
Figure 25:
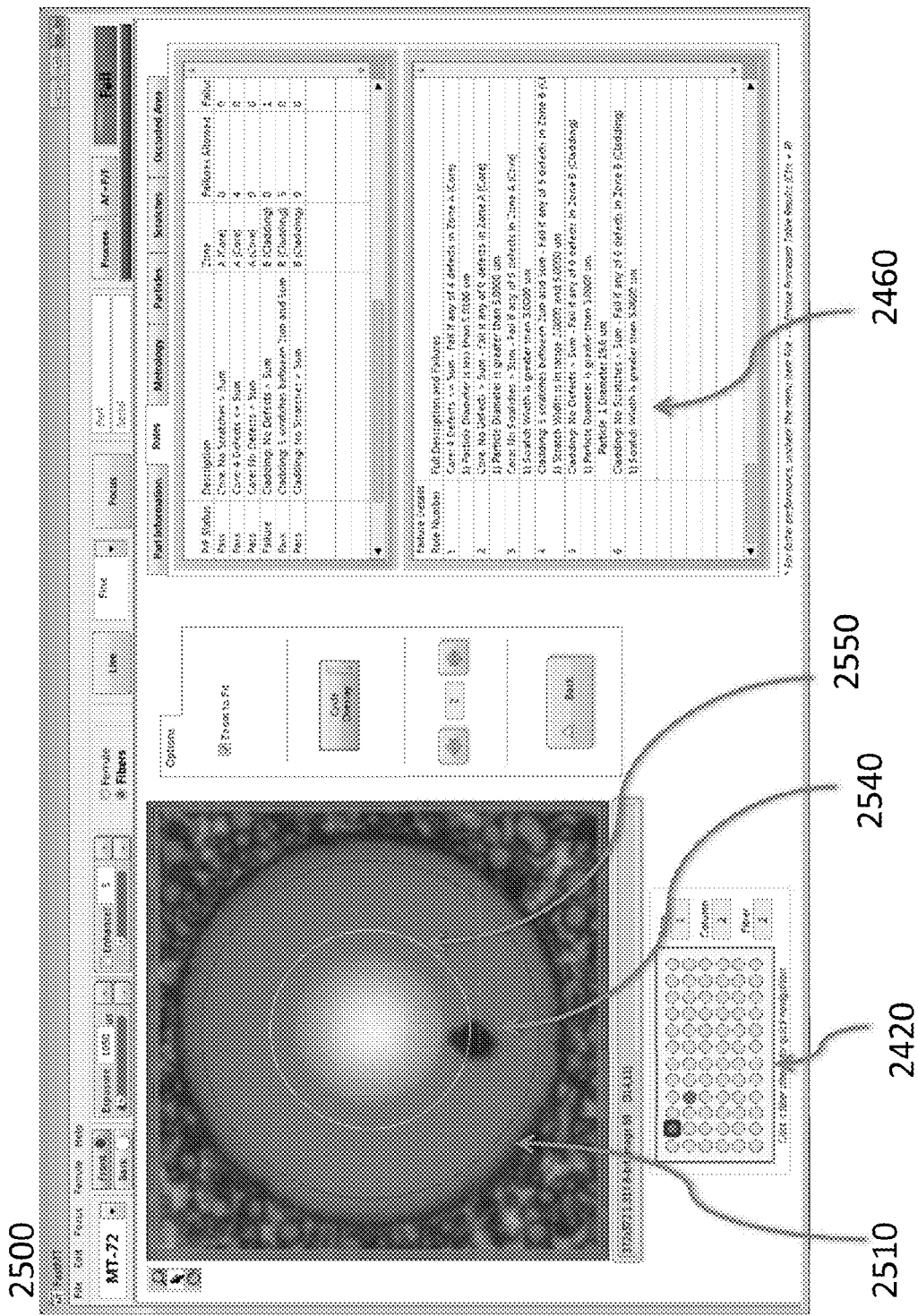
FIG. 25 is an illustration of an automated defect report for a fiber with an identified defect.

FIG. 24 shows an automated defect report 2400 for an individual fiber. The defect report includes a cropped image 2410 of the fiber as captured, wherein a particle defect 2413 is visible. The defect report includes a diagram 2420 of the fiber array showing the inspection results, which may be identified by a color, an outline, a pattern, a shape and the like. The selected fiber being displayed is also highlighted in the diagram 2420 to provide a visual map of the location of the fiber in the array. A description of the defect pass/fail thresholds 2460 being used is also shown. After the cropped image 2410 has been analyzed relative to the defect pass/fail thresholds 2460, another automated defect report is generated 2500 wherein the identified defects are indicated and marked as to pass or fail as shown in FIG. 25. Defect 2540 has been marked as "fail" relative to the defect pass/fail thresholds 2460. In a further embodiment, the defect pass/fail thresholds 2460 can be defined relative to zones in the cropped fiber sub-image. As such, the defect pass/fail thresholds can be more stringent in the center zone than in the outer zone of the fiber. In the cropped sub-image 2510 of the fiber shown in the defect report 2500, where the zones are indicated by rings 2550, such as colored rings.

Figure 26:
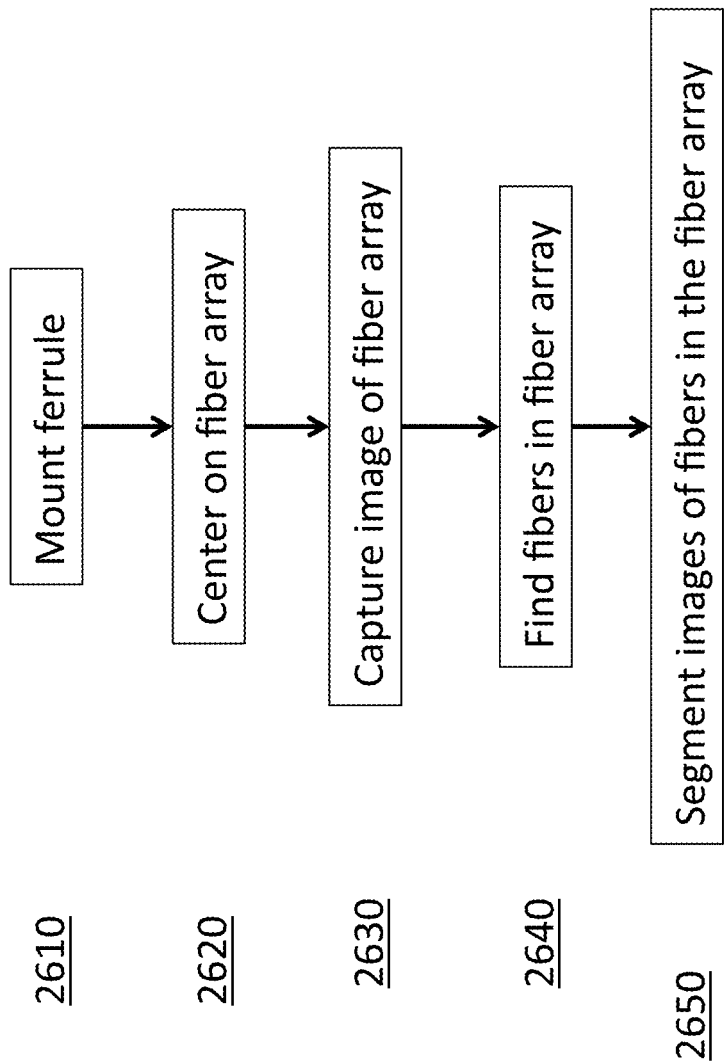
FIG. 26 is a flowchart for a method using a single image of a ferrule.

FIG. 26 is a flowchart for the method of the invention wherein a single image of the fiber array is captured and portions analyzed for each individual fiber in the fiber array to provide a fast and efficient method for inspecting the fiber array. In step 2610, the fiber optic part 1950 or ferrule is mounted into the fixture 1935 of the inspection device assembly 1900. In step 2620, the high-resolution camera 1910 is then centered on the fiber array either based on the known dimensions of the fixture 1935 and the part 1950, or based on an analysis of an image of the fiber array that is captured after the part 1950 is mounted.

In step 2630, the part 1950, is illuminated by the light 1912 and the camera 1910 is autofocused by moving the camera 1910 into focus by the motion control system 1930 and focus quality is measured as previously described. Other methods of autofocus can also be used as previously described. An image of the fiber array is then captured.

In step 2640, the captured image of the fiber array is analyzed to find the fibers in the array. To make it easier to identify the fibers, the captured image may be enhanced to increase the contrast of the fibers relative to the ferrule prior to analysis. The locations of the fibers are then stored and an image with the fibers circled can be provided. Cropped sub-images 2410 of each fiber in the fiber array are then provided wherein the cropped sub-images 2410 are larger than the diameter of the fibers by a user specified percentage. Automatic defect reports such as defect report 2400 or 2500 are then generated for each fiber.

In step 2650, a segmented image 2220 of the fiber array is provided that is comprised of all the cropped sub-images 2400 as captured for the fibers in the fiber array. The cropped sub-images 2400 for all the fibers in the array are linked to the segmented image 2220 so that they can be accessed for subsequent viewing and further analysis. Other segmented images such as 2330 that includes cropped sub-images 2500 that show the results of inspections for defects relative to the defect pass/fail thresholds 2460.

Figure 27:
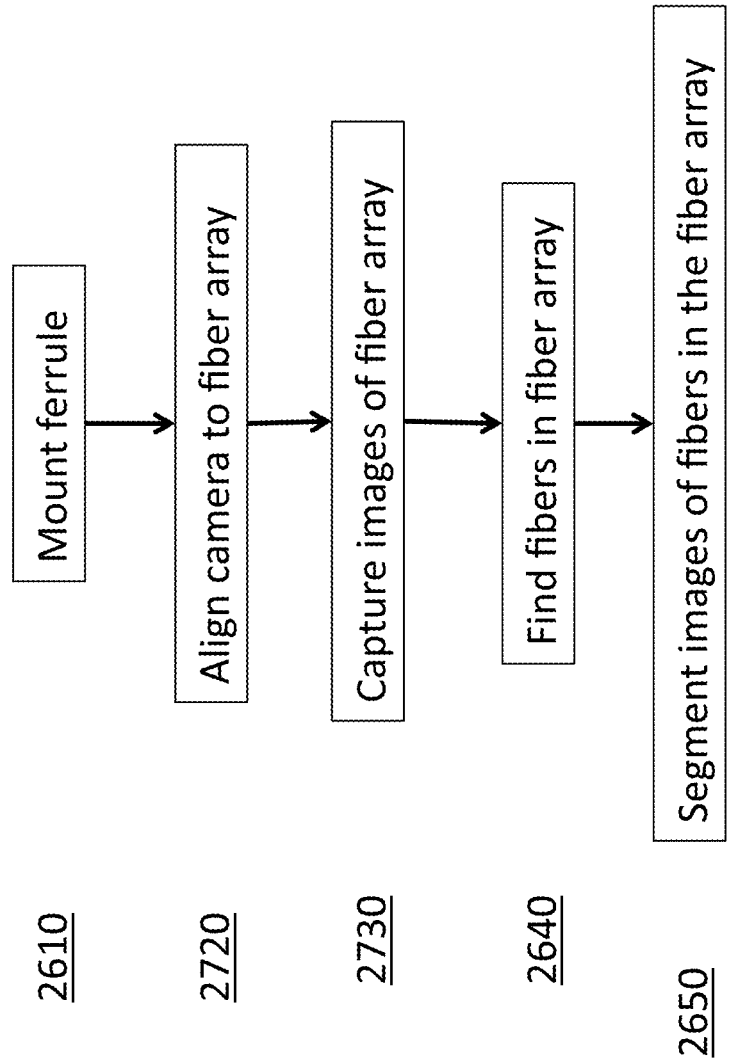
FIG. 27 is a flowchart for a method using multiple adjacent images of a ferrule.

FIG. 27 is a flowchart for the method of the invention wherein the high resolution camera 1910 has a field of view that is smaller than the fiber array so that multiple adjacent sub-images need to be captured to image the entire fiber array. In this process, the camera 1910 has to be moved between multiple positions when capturing the multiple adjacent sub-images such as left sub-image 2105 and right sub-image 2115. This movement involves a lateral movement of the camera 1910 relative to the fiber optic part 1950. The movement is provided by the motion control system 1930. Thus, in this case the motion control system 1930 can include provisions for movement in the X direction for positioning the camera 1910 and the Z direction for focusing the camera onto the fiber array. In the case of a larger fiber array, the motion control system can include provisions for movement in the X and Y direction for positioning the camera for capturing the multiple adjacent images, along with the Z direction for focusing the camera on the fiber array. In step 2720, the motion control system 1930 positions the camera 1910, then in step 2730, the adjacent sub-images of the fiber array are captured. The positioning of the camera and capture of adjacent sub-images is repeated until enough adjacent sub-images have been captured to cover the entire fiber array. The process then proceeds as has been previously described.

In another embodiment, the high resolution camera 1910 and lens 1920 provide a field of view and sufficient resolution to enable entire ferrules to be imaged and defects detected to the defect threshold desired. In this embodiment, the fiber optic part 1950 is comprised of multiple ferrules and the motion control system 1930 moves the camera 1910 and lens 1920 in X and Y directions relative to the fixture 1935 to enable the multiple ferrules in the part to be inspected.

The captured image comprises information on one or more individual fibers along with surrounding ferrule material. In most commonly used connectors, there is a visible degree of contrast between the fiber and the ferrule material. Where the fiber being examined is one of a number in a connector or ferrule being examined such as an MT-Ferrule or V-groove style connector, the captured image may further comprise material such as a glass-filled resin surrounding the individual fibers. These materials may exhibit a reduced level of image contrast. Different lighting in lights 112 or 122 can be used during the image capture to increase the contrast in the captured image to make it easier to identify the fibers.

In another embodiment, segment fibers step 1804, includes cropping sub-images of one or more individual fibers from the captured image of the fiber array and continuing image processing of individually cropped images. One or more of these cropped sub-images containing individual fibers may be processed in parallel to thereby reduce the total elapsed time for processing.

Image processing of the captured images and cropped sub-images can be important to identify fibers and to identify defects. Aspects of image processing 1408 includes pre-process image 1802, segment fibers 1804, detect fibers 1808, and fiber classification 1810.

Pre-process image 1802 is done to optimize or enhance the image prior to image analysis. Pre-process image 1802 may include one or more of the following: removal of a known noise pattern, bad pixel correction, level correction of the image to compensate for brightness fall off or variable reflectivity within the part to be inspected, averaging of multiple acquisitions, and other common processing known in the art to optimize captured image quality. The pre-processing 1802 may also include verification of image quality including focus, proper illumination, and the like. In an embodiment of the system, the system may automatically adjust focus, illumination, and the like, reacquire the image and pre-process 1802 the newly acquired image before proceeding with additional image processing.

Upon completion of preprocess image 1802, segment fibers 1804 may include one or more steps such as upsampling the image, contrast enhancement, application of simple threshold segmentation, and the like to differentiate a fiber from the surrounding material.

Once an individual fiber is identified, the process of detecting defects 1808 may include identifying the center of the fiber, detecting the edge of the fiber, detecting scratches, pits, chips, cracks, spots, streaks, loose contamination and other flaws on the fiber face, and the like. Additional data may include concentricity of the core to cladding and other 2D geometric parameters such as diameters, circularity and the like. Data regarding each individual defect is calculated comprising location of defect, size of defect, and contrast. Additional data may be calculated for the total fiber including one or more of the following: total or percent area occluded, or total or percent occlusion in a particular region of the fiber and the like. The fiber image, overlaid with highlighting indications of defects (such as colored circles or lines) and defect data may be stored in a file or database or the like for future review.

Fiber classification 1810 may further include the comparing defect data obtained to specified pass-fail criteria. The pass-fail criteria may comprise a common industry standard or custom criteria set at the user interface 1402. The particular fiber may then be classified as pass or fail.

Figure 16:
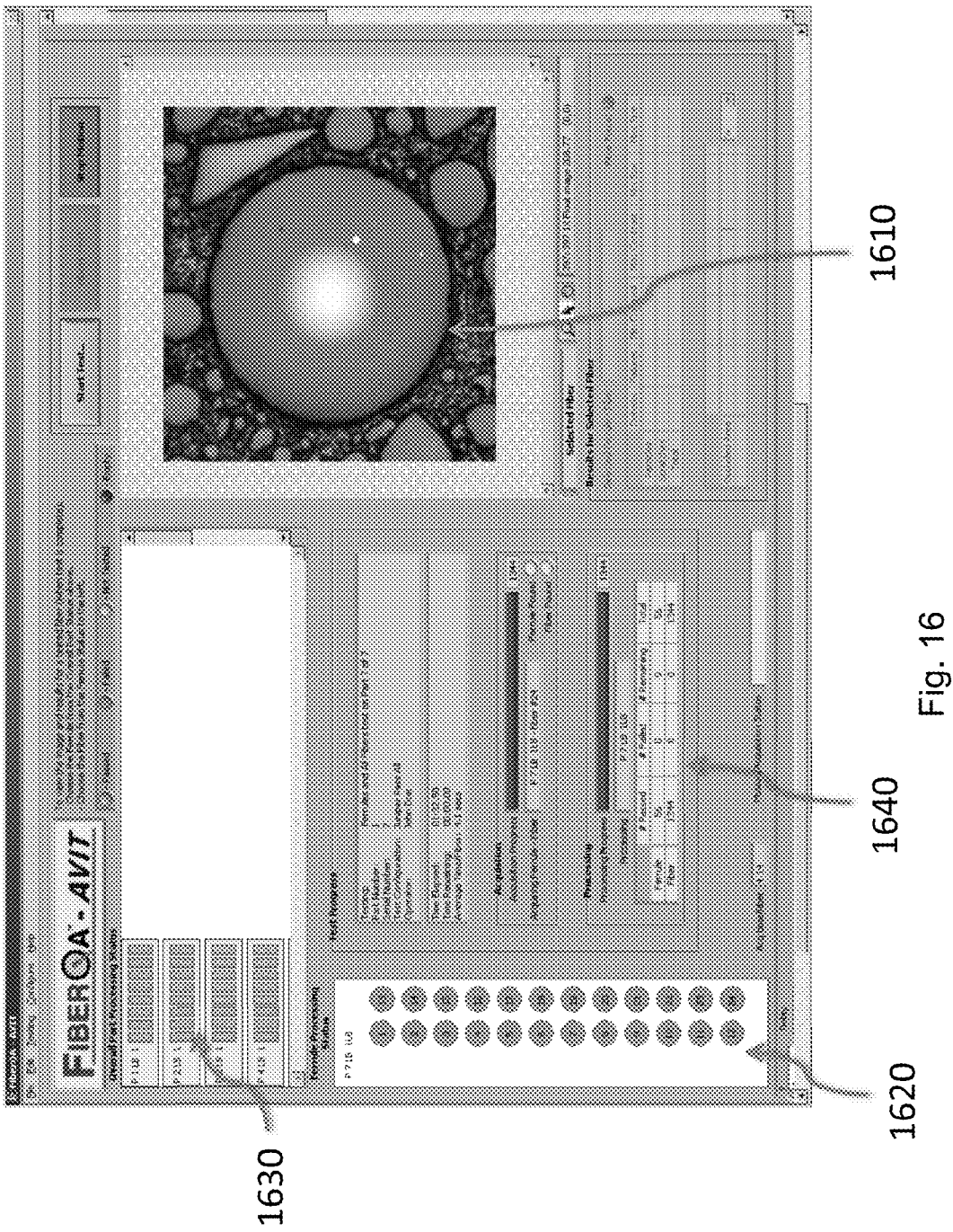
FIG. 16 depicts a user interface for automated inspection and cleaning of a part having multiple ferrules.
Figure 18:
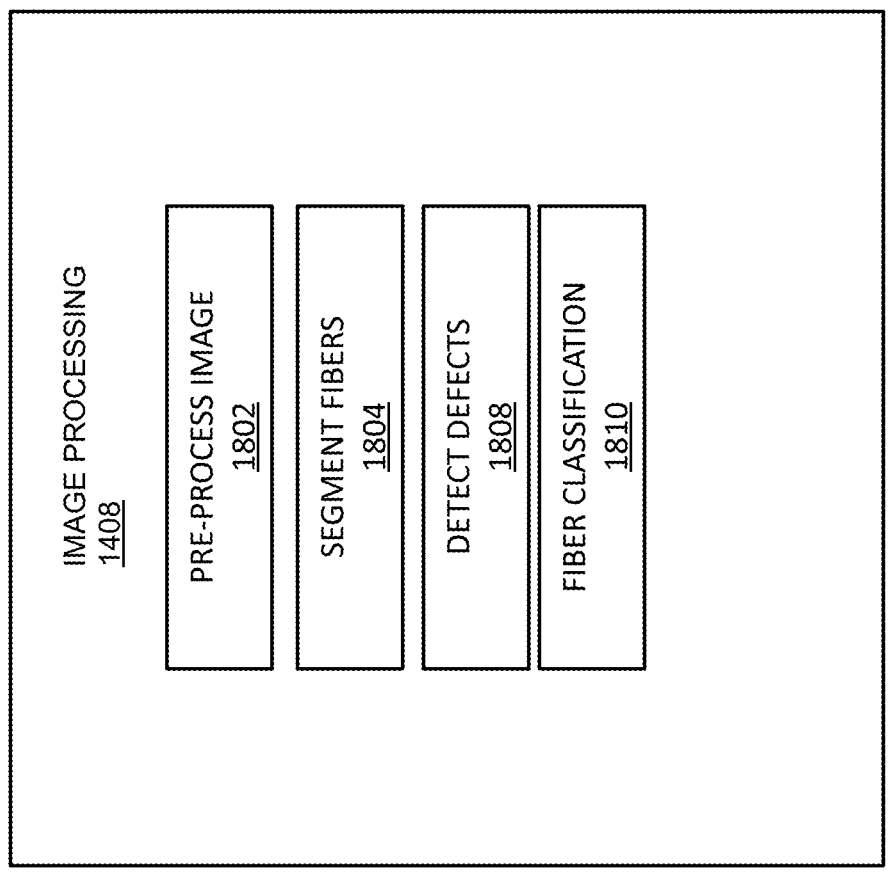
FIG. 18 depicts an image processing workflow.

In another embodiment, there may be an ability to abort the image processing 1408 prior to the completion of inspecting of all the fibers if the number of failed fibers or ferrules exceeds a specified pass-fail criteria The user interface 1402 may further include a means for displaying results including one or more of the following: displaying the image as examined, displaying an image with overlaid highlighting indications of defects, indication of pass/fail status and data describing the type, location and area of individual defects, and the like. FIG. 16 shows an example of a user interface for an automatically generated pass/fail report page for a fiber array in a ferrule during an automated defect inspection and cleaning. A high magnification image 1610 of the fiber being tested is shown for reference. A diagram of the ferrule 1620 being inspected is provided that shows the fiber array wherein the individual fibers that passed/failed the defect inspection are indicated by color such as green for pass and red for fail (all the fibers are indicated as passing in this example). Colored markings (not shown in FIG. 16) related to identified defects can be overlaid onto the image of the fiber 1610 for further reference. The tested results for the entire part 1630 are shown as well, where the part is comprised of multiple ferrules. Information related to the progress of the current test is shown in a table 1640.

In addition, the results may be saved including raw image, defect overlaid image, identified defects and associated information, pass-fail status, and the like, may also be stored in a file, database or the like.

The user interface 1402 may also include the ability to generate reports 1512 including one or more of the following: images and data for review after tests are complete, the ability to select and report individual test results from a list of test results, the ability to export results of one or more tests to a spreadsheet, database or other like format, aggregate test results, individual and multiple images, process tracking data, and the like.

The methods and systems described herein may be deployed in part or in whole through a machine that executes computer software, program codes, and/or instructions on a processor. The processor may be part of a server, cloud server, client, network infrastructure, mobile computing platform, stationary computing platform, or other computing platform. A processor may be any kind of computational or processing device capable of executing program instructions, codes, binary instructions and the like. The processor may be or include a signal processor, digital processor, embedded processor, microprocessor or any variant such as a co-processor (math co-processor, graphic co-processor, communication co-processor and the like) and the like that may directly or indirectly facilitate execution of program code or program instructions stored thereon. In addition, the processor may enable execution of multiple programs, threads, and codes. The threads may be executed simultaneously to enhance the performance of the processor and to facilitate simultaneous operations of the application. By way of implementation, methods, program codes, program instructions and the like described herein may be implemented in one or more thread. The thread may spawn other threads that may have assigned priorities associated with them; the processor may execute these threads based on priority or any other order based on instructions provided in the program code. The processor may include memory that stores methods, codes, instructions and programs as described herein and elsewhere. The processor may access a storage medium through an interface that may store methods, codes, and instructions as described herein and elsewhere. The storage medium associated with the processor for storing methods, programs, codes, program instructions or other type of instructions capable of being executed by the computing or processing device may include but may not be limited to one or more of a CD-ROM, DVD, memory, hard disk, flash drive, RAM, ROM, cache and the like.

A processor may include one or more cores that may enhance speed and performance of a multiprocessor. In embodiments, the process may be a dual core processor, quad core processors, other chip-level multiprocessor and the like that combine two or more independent cores (called a die).

The methods and systems described herein may be deployed in part or in whole through a machine that executes computer software on a server, client, firewall, gateway, hub, router, or other such computer and/or networking hardware. The software program may be associated with a server that may include a file server, print server, domain server, internet server, intranet server and other variants such as secondary server, host server, distributed server and the like. The server may include one or more of memories, processors, computer readable media, storage media, ports (physical and virtual), communication devices, and interfaces capable of accessing other servers, clients, machines, and devices through a wired or a wireless medium, and the like. The methods, programs or codes as described herein and elsewhere may be executed by the server. In addition, other devices required for execution of methods as described in this application may be considered as a part of the infrastructure associated with the server.

The server may provide an interface to other devices including, without limitation, clients, other servers, printers, database servers, print servers, file servers, communication servers, distributed servers, social networks, and the like. Additionally, this coupling and/or connection may facilitate remote execution of program across the network. The networking of some or all of these devices may facilitate parallel processing of a program or method at one or more location without deviating from the scope of the invention. In addition, any of the devices attached to the server through an interface may include at least one storage medium capable of storing methods, programs, code and/or instructions. A central repository may provide program instructions to be executed on different devices. In this implementation, the remote repository may act as a storage medium for program code, instructions, and programs.

The software program may be associated with a client that may include a file client, print client, domain client, internet client, intranet client and other variants such as secondary client, host client, distributed client and the like. The client may include one or more of memories, processors, computer readable media, storage media, ports (physical and virtual), communication devices, and interfaces capable of accessing other clients, servers, machines, and devices through a wired or a wireless medium, and the like. The methods, programs or codes as described herein and elsewhere may be executed by the client. In addition, other devices required for execution of methods as described in this application may be considered as a part of the infrastructure associated with the client.

The client may provide an interface to other devices including, without limitation, servers, cloud servers, other clients, printers, database servers, print servers, file servers, communication servers, distributed servers and the like. Additionally, this coupling and/or connection may facilitate remote execution of program across the network. The networking of some or all of these devices may facilitate parallel processing of a program or method at one or more location without deviating from the scope of the invention. In addition, any of the devices attached to the client through an interface may include at least one storage medium capable of storing methods, programs, applications, code and/or instructions. A central repository may provide program instructions to be executed on different devices. In this implementation, the remote repository may act as a storage medium for program code, instructions, and programs.

The methods and systems described herein may be deployed in part or in whole through network infrastructures. The network infrastructure may include elements such as computing devices, servers, cloud servers, routers, hubs, firewalls, clients, personal computers, communication devices, routing devices and other active and passive devices, modules and/or components as known in the art. The computing and/or non-computing device(s) associated with the network infrastructure may include, apart from other components, a storage medium such as flash memory, buffer, stack, RAM, ROM and the like. The processes, methods, program codes, instructions described herein and elsewhere may be executed by one or more of the network infrastructural elements.

The methods, program codes, and instructions described herein and elsewhere may be implemented on a cellular network having multiple cells. The cellular network may either be frequency division multiple access (FDMA) network or code division multiple access (CDMA) network. The cellular network may include mobile devices, cell sites, base stations, repeaters, antennas, towers, and the like. The cell network may be a GSM, GPRS, 3G, EVDO, mesh, or other networks types.

The methods, programs codes, and instructions described herein and elsewhere may be implemented on or through mobile devices. The mobile devices may include navigation devices, cell phones, mobile phones, mobile personal digital assistants, laptops, palmtops, netbooks, pagers, electronic books readers, music players and the like. These devices may include, apart from other components, a storage medium such as a flash memory, buffer, RAM, ROM and one or more computing devices. The computing devices associated with mobile devices may be enabled to execute program codes, methods, and instructions stored thereon. Alternatively, the mobile devices may be configured to execute instructions in collaboration with other devices. The mobile devices may communicate with base stations interfaced with servers and configured to execute program codes. The mobile devices may communicate on a peer to peer network, mesh network, or other communications network. The program code may be stored on the storage medium associated with the server and executed by a computing device embedded within the server. The base station may include a computing device and a storage medium. The storage device may store program codes and instructions executed by the computing devices associated with the base station.

The computer software, program codes, and/or instructions may be stored and/or accessed on machine readable media that may include: computer components, devices, and recording media that retain digital data used for computing for some interval of time; semiconductor storage known as random access memory (RAM); mass storage typically for more permanent storage, such as optical discs, forms of magnetic storage like hard disks, tapes, drums, cards and other types; processor registers, cache memory, volatile memory, non-volatile memory; optical storage such as CD, DVD; removable media such as flash memory (e.g. USB sticks or keys), floppy disks, magnetic tape, paper tape, punch cards, standalone RAM disks, Zip drives, removable mass storage, off-line, and the like; other computer memory such as dynamic memory, static memory, read/write storage, mutable storage, read only, random access, sequential access, location addressable, file addressable, content addressable, network attached storage, storage area network, bar codes, magnetic ink, and the like.

The methods and systems described herein may transform physical and/or or intangible items from one state to another. The methods and systems described herein may also transform data representing physical and/or intangible items from one state to another.

The elements described and depicted herein, including in flow charts and block diagrams throughout the figures, imply logical boundaries between the elements. However, according to software or hardware engineering practices, the depicted elements and the functions thereof may be implemented on machines through computer executable media having a processor capable of executing program instructions stored thereon as a monolithic software structure, as standalone software modules, or as modules that employ external routines, code, services, and so forth, or any combination of these, and all such implementations may be within the scope of the present disclosure. Examples of such machines may include, but may not be limited to, personal digital assistants, laptops, personal computers, mobile phones, other handheld computing devices, medical equipment, wired or wireless communication devices, transducers, chips, calculators, satellites, tablet PCs, electronic books, gadgets, electronic devices, devices having artificial intelligence, computing devices, networking equipment, servers, routers and the like. Furthermore, the elements depicted in the flow chart and block diagrams or any other logical component may be implemented on a machine capable of executing program instructions. Thus, while the foregoing drawings and descriptions set forth functional aspects of the disclosed systems, no particular arrangement of software for implementing these functional aspects should be inferred from these descriptions unless explicitly stated or otherwise clear from the context. Similarly, it will be appreciated that the various steps identified and described above may be varied, and that the order of steps may be adapted to particular applications of the techniques disclosed herein. All such variations and modifications are intended to fall within the scope of this disclosure. As such, the depiction and/or description of an order for various steps should not be understood to require a particular order of execution for those steps, unless required by a particular application, or explicitly stated or otherwise clear from the context.

The methods and/or processes described above, and steps thereof, may be realized in hardware, software or any combination of hardware and software suitable for a particular application. The hardware may include a general purpose computer and/or dedicated computing device or specific computing device or particular aspect or component of a specific computing device. The processes may be realized in one or more microprocessors, microcontrollers, embedded microcontrollers, programmable digital signal processors or other programmable device, along with internal and/or external memory. The processes may also, or instead, be embodied in an application specific integrated circuit, a programmable gate array, programmable array logic, or any other device or combination of devices that may be configured to process electronic signals. It will further be appreciated that one or more of the processes may be realized as a computer executable code capable of being executed on a machine readable medium.

The computer executable code may be created using a structured programming language such as C, an object oriented programming language such as C++, or any other high-level or low-level programming language (including assembly languages, hardware description languages, and database programming languages and technologies) that may be stored, compiled or interpreted to run on one of the above devices, as well as heterogeneous combinations of processors, processor architectures, or combinations of different hardware and software, or any other machine capable of executing program instructions.

Thus, in one aspect, each method described above and combinations thereof may be embodied in computer executable code that, when executing on one or more computing devices, performs the steps thereof. In another aspect, the methods may be embodied in systems that perform the steps thereof, and may be distributed across devices in a number of ways, or all of the functionality may be integrated into a dedicated, standalone device or other hardware. In another aspect, the means for performing the steps associated with the processes described above may include any of the hardware and/or software described above. All such permutations and combinations are intended to fall within the scope of the present disclosure.

While the invention has been disclosed in connection with the preferred embodiments shown and described in detail, various modifications and improvements thereon will become readily apparent to those skilled in the art. Accordingly, the spirit and scope of the present invention is not to be limited by the foregoing examples, but is to be understood in the broadest sense allowable by law.

All documents referenced herein are hereby incorporated by reference.

PARTS LIST

100 cleaning and inspection head assembly
105 electronics
110 ferrule camera
112 light
114 wide FOV lens 120 fiber camera
122 light
124 narrow FOV lens
130 cleaning tip
132 cleaning module
200 cleaning module assembly
240 cleaning media controller
250 force controller
300 cleaning tip assembly
360 cleaning tip extension
365 cleaning tip
367 cleaning media
369 media guide slot
400 cleaning and inspection device
470 case
471 test chamber
472 fiber optic connectors
474 connector test plate
476 test plate rack
478 rack mount
580 fiber optic connector
581 alignment hole
582 fiber optic array
583 ferrule
682 fiber optic array
683 ferrule
780 fiber optic connector
782 fiber optic
783 ferrule
882 fiber optic array
890 general cleaning path
892 overlaid circular cleaning path
894 general cleaning path
982 dirty fiber optic
983 cleaned fiber optic
985 debris
987 spots
1001 defect as captured
1002 defect with enhanced contrast
1003 identified defect
1210 image of ferrule being inspected
1220 diagram of a ferrule being inspected that shows test results by fiber
1230 diagram of entire part showing results by ferrule
1240 information related to the test being conducted
1310 mounting step
1320 determine locations step
1330 cleaning step
1340 inspecting step
1342 identifying defects step
1343 fiber OK step
1350 identifying defects step
1352 cleaning step
1360 generate assessment step
1400 processor
1402 user interface
1404 image capture
1408 image processing
1502 calibrate system step
1504 specify inspection criteria step
1508 optimize image capture step
1510 display results step
1512 generate reports step
1610 high magnification image of fiber being tested
1620 diagram of the ferrule being inspected for defects showing results for each fiber
1630 diagram of entire part showing results for each ferrule
1640 information related to ongoing inspections
1700 sample specification of inspection criteria
1802 pre-process image step
1804 segment fibers step
1808 detect defects step
1810 fiber classification step
1900 inspection device assembly
1905 electronics
1910 high resolution camera
1912 light
1920 high resolution lens
1930 motion system
1935 fixture
1950 fiber optic part
2082 fiber optic array with identified fibers circled
2105 left subimage of fiber array
2115 right subimage of fiber array
2220 segmented image of fiber array with cropped images as captured
2225 cropped image of fiber as captured
2330 segmented image of fiber array with cropped images of fibers showing inspection results
2335 cropped image of fiber showing failure due to defect
2410 image of fiber as captured
2413 visible defect in fiber
2420 diagram of fiber array showing inspection results
2510 image of fiber with overlaid zones and identified defect circled
2540 circled identified defect
2550 defect zone markers
2610 mount ferrule in fixture step
2620 center the camera on the fiber array step
2630 capture image of fiber array step
2640 find fibers in fiber array step
2650 segment images of fibers in the fiber array step
2720 align camera to fiber array step
2730 capture images of fiber array step

What is claimed is:

1. A system for optical fiber end face inspection, comprising:
a camera adapted to capture an image of an optical fiber end face region of a ferrule for inspection, wherein, with an autofocus facility, the camera automatically focuses to a level required for one or more of: a) imaging the number of optical fiber end faces present in the ferrule, and b) detecting defects of a certain size;
a processor adapted to display the captured image of the optical fiber end face region on a display screen, wherein the processor automatically adjusts the display of the captured image on the display screen to accommodate the number of optical fiber end faces in the captured image; and
wherein the processor is further adapted to analyze the captured image of the optical fiber end face region to determine a presence of a defect, wherein the processor analyzes the captured image to identify each individual optical fiber end face therein from a surrounding material of the ferrule, segments the captured image to produce a plurality of sub-images, each sub-image including a respective one of the identified individual optical fiber end faces, and re-assembles the plurality of sub-images for display as a fiber-by-fiber view.

2. The system of claim 1, wherein the camera is adapted to zoom in on identified individual optical fiber end faces to enable a visual inspection and evaluation.

3. The system of claim 1, wherein the display screen further presents an inspection report of the plurality of sub-images, wherein the inspection report indicates at least which optical fiber end faces have a defect.

4. The system of claim 1, wherein the processor processes at least some of the plurality of sub-images in parallel to determine the presence of a defect.

5. The system of claim 3, wherein the inspection report indicates which optical fiber end faces have a defect by outlining a sub-image with a colored box.

6. The system of claim 4, wherein once a threshold of defect detection is reached, the processor aborts further parallel processing and performs one or more of: failing the ferrule and initiating a cleaning step.

7. The system of claim 6, wherein the threshold of defect detection is user customizable.

8. The system of claim 6, wherein the threshold of defect detection is determined by an industry standard.

9. A system for optical fiber end face inspection, comprising:
- a camera adapted to capture an image of an optical fiber end face region of a ferrule for inspection, wherein, with an autofocus facility, the camera automatically focuses to a level required for one or more of: a) imaging the number of optical fiber end faces present in the ferrule, and b) detecting defects of a certain size;
- a processor adapted to display the captured image of the optical fiber end face region on a display screen, wherein the processor automatically adjusts the display of the captured image on the display screen to accommodate the number of optical fiber end faces in the captured image, the processor further adapted to analyze the captured image of an optical fiber end face region to determine a presence of a defect, wherein the processor analyzes the captured image to identify each individual optical fiber end face therein from a surrounding material of the ferrule, segments the captured image to produce a plurality of sub-images, each sub-image including a respective one of the identified individual optical fiber end faces, and re-assembles the plurality of sub-images for display as a fiber-by-fiber view; and
- a cleaning module adapted to clean the optical fiber end face region, wherein the cleaning module comprises a tip with a cleaning medium that is moved relative to the optical fiber end face region.

10. The system of claim 9, wherein the camera is adapted to zoom in on identified individual optical fiber end faces to enable a visual inspection and evaluation.

11. The system of claim 9, wherein the display screen further presents an inspection report of the plurality of sub-images, wherein the inspection report indicates at least which optical fiber end faces have a defect.

12. The system of claim 9, wherein the processor processes at least some of the plurality of sub-images in parallel to determine the presence of defect.

13. The system of claim 11, wherein the inspection report indicates which optical fiber end faces have a defect by outlining a sub-image with a colored box.

14. The system of claim 12, wherein once a threshold of defect detection is reached, the processor aborts further parallel processing and performs one or more of failing the ferrule and initiating a cleaning step.

15. The system of claim 14, wherein the threshold of defect detection is user customizable.

16. The system of claim 14, wherein the threshold of defect detection is determined by an industry standard.

17. A system for optical fiber end face inspection, comprising:
- a camera adapted to capture an image of an optical fiber end face region of a ferrule for inspection, wherein, with an autofocus facility, the camera automatically focuses to a level required for one or more of: a) imaging the number of optical fiber end faces present in the ferrule, and b) detecting defects of a certain size;
- a processor adapted to display the captured image of the optical fiber end face region on a display screen, wherein the processor automatically adjusts the display of the captured image on the display screen to accommodate the number of optical fiber end faces in the captured image; and
- a cleaning module adapted to clean the optical fiber end face region, wherein the cleaning module comprises a tip with a cleaning medium that is moved relative to the optical fiber end face region to clean the optical fiber;
- wherein the processor is further adapted to analyze the captured image of the optical fiber end face region to determine a presence of a defect, wherein the optical fiber end face region is an array of optical fiber end faces, and wherein the tip is moved in an oscillatory movement that begins at one corner of the array of optical fiber end faces, crosses the array and ends at an adjacent corner of the array.

18. A system for optical fiber end face inspection, comprising:
- a camera adapted to capture an image of an optical fiber end face region of a ferrule for inspection, wherein, with an autofocus facility, the camera automatically focuses to a level required for one or more of: a) imaging the number of optical fiber end faces present in the ferrule, and b) detecting defects of a certain size;
- a processor adapted to display the captured image of the optical fiber end face region on a display screen, wherein the processor automatically adjusts the display of the captured image on the display screen to accommodate the number of optical fiber end faces in the captured image; and
- a cleaning module adapted to clean the optical fiber end face region, wherein the cleaning module comprises a tip with a cleaning medium that is moved relative to the optical fiber end face region to clean the optical fiber;
- wherein the processor is further adapted to analyze the captured image of the optical fiber end face region to determine a presence of a defect, wherein the optical fiber end face region is an array of optical fiber end faces, and wherein the tip is moved in a line down the array of optical fiber end faces combined with an overlaid circular cleaning path.

* * * * *